(12) United States Patent
Yamamoto et al.

(10) Patent No.: US 11,407,709 B2
(45) Date of Patent: Aug. 9, 2022

(54) ARYLDIAMINE COMPOUND AND ORGANIC ELECTROLUMINESCENT ELEMENT

(71) Applicant: HODOGAYA CHEMICAL CO., LTD., Tokyo (JP)

(72) Inventors: Takeshi Yamamoto, Tokyo (JP); Kouki Kase, Tokyo (JP); Shunji Mochiduki, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 351 days.

(21) Appl. No.: 16/328,619

(22) PCT Filed: Sep. 7, 2017

(86) PCT No.: PCT/JP2017/032239
§ 371 (c)(1),
(2) Date: Feb. 26, 2019

(87) PCT Pub. No.: WO2018/047899
PCT Pub. Date: Mar. 15, 2018

(65) Prior Publication Data
US 2020/0231534 A1  Jul. 23, 2020

(30) Foreign Application Priority Data
Sep. 9, 2016  (JP) ............... JP2016-176349

(51) Int. Cl.
*C07C 211/54* (2006.01)
*C07C 211/61* (2006.01)
(Continued)

(52) U.S. Cl.
CPC .......... *C07C 211/54* (2013.01); *C07C 211/61* (2013.01); *H01L 51/006* (2013.01); *H01L 51/5012* (2013.01); *H01L 51/5056* (2013.01)

(58) Field of Classification Search
CPC .. C07C 211/51; C07C 211/54; H01L 51/0059
See application file for complete search history.

(56) References Cited

U.S. PATENT DOCUMENTS 5,494,765 A * 2/1996 Fukami ............... G03G 5/0609
430/58.75
5,780,194 A * 7/1998 Katsukawa ............ G03G 5/056
430/83

(Continued)

FOREIGN PATENT DOCUMENTS

CN  101282931 A  10/2008
JP  8-286398 A  11/1996
(Continued)

OTHER PUBLICATIONS

SciFinder Search (Year: 2021).*
(Continued)

*Primary Examiner* — Vu A Nguyen
(74) *Attorney, Agent, or Firm* — Birch, Stewart, Kolasch & Birch, LLP

(57) ABSTRACT

An aryldiamine compound represented by formula (1) and an organic electroluminescent device including a pair of electrodes and at least one organic layer disposed therebetween wherein the at least one organic layer contains the aryldiamine compound. The aryldiamine compound is excellent in hole transporting properties, hole injection properties, electron blocking properties, stability in thin film form, and heat resistance. The organic electroluminescent device achieves high emission efficiency and power efficiency, drives at a low voltage, and, in particular, has a long life.

(Continued)

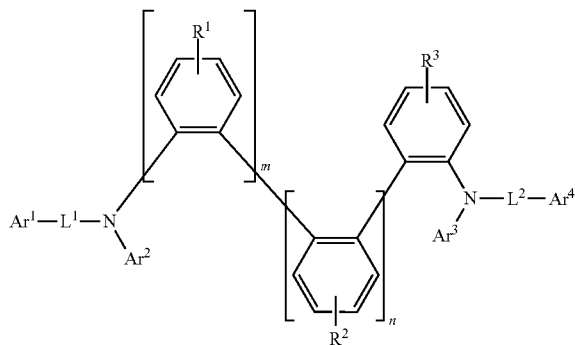

(1)

7 Claims, 14 Drawing Sheets

(51) Int. Cl.
*H01L 51/00* (2006.01)
*H01L 51/50* (2006.01)

(56) References Cited

U.S. PATENT DOCUMENTS

2014/0339518 A1* 11/2014 Yamamoto .......... H01L 51/5016
257/40
2015/0380656 A1 12/2015 Sakamoto

FOREIGN PATENT DOCUMENTS

| JP | 3194657-82 | | 7/2001 | |
|---|---|---|---|---|
| JP | 2006-156635 | A | 6/2006 | |
| JP | 3828595 | B2 | 10/2006 | |
| JP | 2008-133225 | A | 6/2008 | |
| JP | 2009-170810 | A | 7/2009 | |
| JP | 4770033 | B2 | 9/2011 | |
| JP | 2016-12676 | A | 1/2016 | |
| JP | 2017-165722 | A | 9/2017 | |
| KR | 20160113783 | A * | 10/2016 | |
| KR | 10-1686835 | B1 | 12/2016 | |
| KR | 10-2017-0037135 | A | 4/2017 | |
| KR | 20170037135 | A * | 4/2017 | |
| WO | WO 2014/060526 | A1 | 4/2014 | |
| WO | WO 2016/167491 | A1 | 10/2016 | |
| WO | WO 2017/043835 | A1 | 3/2017 | |
| WO | WO-2017043835 | A1 * | 3/2017 | .......... C07D 333/76 |

OTHER PUBLICATIONS

Computer-generated English-language translation of WO-2017043835-A1.*
Computer-generated English-language translation of KR-20160113783-A.*
Computer-generated English-language translation of KR-20170037135-A.*
International Search Report (PCT/ISA/210) issued in PCT/JP2017/032239, dated Oct. 31, 2017.
Liou et al., "Synthesis and Evaluation of Photoluminescent and Electrochemical Properties of New Aromatic Polyamides and Polyimides with a Kink 1,2-Phenylenediamine Moiety", Journal of Polymer Science, PartA: Polymer Chemistry, 2006, vol. 44, No. 8, pp. 2587-2603, Scheme 1.
Nöll et al., "Optically induced electron transfer in an N,N,N',N'-tereaanisyl-o-phenlendediamine radical cation", Journal of Physical Organic Chemistry, 2006, vol. 19, No. 4, pp. 238-241, p. 238, right column.

* cited by examiner (1-31)

(1-32)

(2-9)

(2-10)

(2-11)

(2-12)

(2-13)

(2-14)

(2-15)

(2-16)

(2-31)

(2-32)

(2-33)

(2-34)

(2-35)

(2-36)

ARYLDIAMINE COMPOUND AND ORGANIC ELECTROLUMINESCENT ELEMENT

TECHNICAL FIELD

This invention relates to a compound suited for use in an organic electroluminescent device (hereinafter referred to as an organic EL device) and an organic EL device. More particularly, it relates to a specific aryldiamine compound and an organic EL device using the compound.

BACKGROUND ART

An organic EL device is self-luminescent, so that the organic EL device enables brighter, more visible, and clearer image display than liquid crystal devices and has therefore been studied extensively.

C. W. Tang, et al. of Eastman Kodak developed a stacked device having a plurality of materials each performing its own role in 1987 and put an organic EL device using organic materials to practical use. An organic EL device is fabricated by stacking a fluorescent substance capable of transporting electrons and an organic substance capable of transporting holes. The opposite charges are injected to the emitting layer of the fluorescent substance to emit light, whereby a luminance as high as 1000 cd/m$^2$ or even higher is obtained at a voltage of 10 V or lower (see patent literatures 1 and 2 below).

A number of improvements have so far been added to existing organic EL devices with a view to practical use. For example, the roles of the stacked layers are further divided such that the EL device is composed of a substrate, an anode, a hole injection layer, a hole transport layer, an emitting layer, an electron transport layer, an electron injection layer, and a cathode stacked in that order. Such a structure has been achieving high efficiency and durability.

With the view of further improvement of emission efficiency, use of triplet excitons has been attempted, and studies have been directed to use of phosphorescent compounds. Devices utilizing emission by thermally activated delayed fluorescence (TADF) have also been under development. Adachi, et al. of Kyusyu University achieved an external quantum efficiency of 5.3% by their device comprising a TADF material in 2011.

An emitting layer is generally formed by doping a charge transport compound called a host material with a fluorescent compound, a phosphorescent compound, or a delayed fluorescence emitter. Choice of an organic material is largely influential on various characteristics of organic EL devices, such as efficiency and durability.

Luminescence by organic EL devices is obtained by recombination of charges injected from the respective electrodes in the emitting layer. Therefore, how efficiently the opposite charges (i.e., holes and electrons) are transported to the emitting layer is important in organic EL devices, and the EL devices should have a good charge carrier balance. The probability of recombination of holes and electrons will increase with enhancement of hole injection and enhancement of electron blocking (the ability of stopping electrons injected from the cathode), and high emission efficiency will be obtained by confining the excitons in the emitting layer.

The role to be performed by the hole transport material is of significance. Thus, a hole transport material having high hole injection ability, high hole mobility, high electron blocking ability, and high durability to electrons has been sought.

From the viewpoint of device service life, the heat resistance and amorphous properties of materials are also important. Low heat-resistant materials decompose thermally, even in low temperatures, due to the heat generated on driving the device and eventually deteriorate. Materials with low amorphous properties crystallize in a short time in thin film form, thereby deteriorating the device. Hence, materials to be used are required to have high heat resistance and good amorphous properties.

Hole transport materials known for use in organic EL devices include N,N'-diphenyl-N,N'-di(α-naphthyl)benzidine (NPD) and various aromatic amine derivatives (see patent literatures 1 and 2). Although NPD exhibits good hole transporting properties, its glass transition temperature (Tg), which is a measure of heat resistance, is as low as 96° C. so that the device characteristics can reduce in a high temperature atmosphere due to crystallization. Some of the aromatic amine derivatives disclosed in patent literatures 1 and 2 exhibit hole mobility as high as $10^{-3}$ cm$^2$/Vs or higher but have insufficient electron blocking ability. Organic EL devices using such aromatic amine derivatives allow part of electrons to pass through the emitting layer and, therefore, no improvement on emission efficiency is expected. Accordingly, a material having higher electron blocking ability, higher stability in thin film form, and higher heat resistance has been demanded.

Aromatic tertiary amine compounds represented by the following formulae have been proposed for the improvements on such characteristics as heat resistance, hole injecting properties, hole transporting properties, and electron blocking properties (see patent literatures 3 and 4 below).

[Chem.1]

(Compound A)

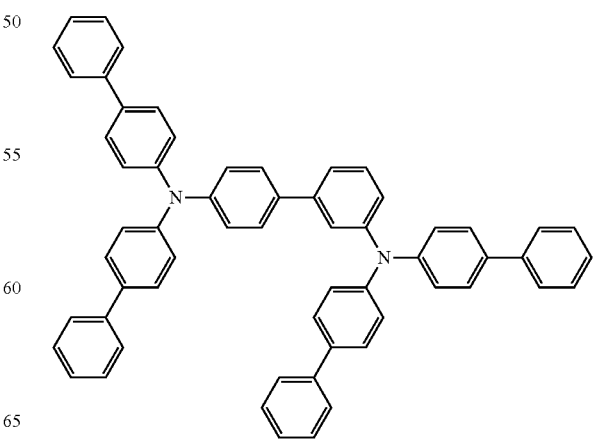

-continued

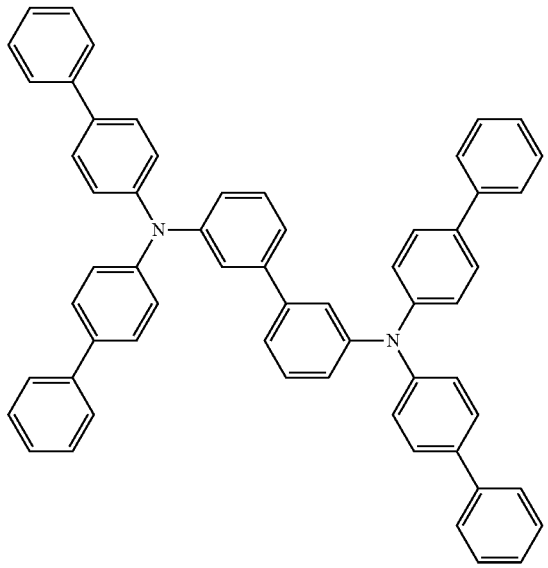

(Compound B)

While devices using these compounds in the hole injection layer, hole transport layer, or electron blocking layer show improvements on heat resistance and emission efficiency, the effects obtained are still insufficient, and further reduction of driving voltage and higher emission efficiency have been demanded.

In order to improve device characteristics of organic EL devices, an organic EL device having high efficiency based on good carrier balance, a low driving voltage, and a long life could be obtained by combining materials having excellent hole injecting properties, hole transporting properties, electron injecting properties, electron transporting properties, stability in thin film form, and durability.

CITATION LIST

Patent Literature

Patent literature 1: JP 3828595
Patent literature 2: JP 3194657
Patent literature 3: JP 4770033
Patent literature 4: WO 2014/060526

SUMMARY OF INVENTION

Technical Problem

An object of the invention is to provide, as a material for high-efficient and high-durable organic EL device, an aryldiamine compound having (1) excellent hole transporting properties, (2) stability in thin film form, and (3) high heat resistance.

Another object of the invention is to provide an organic EL device having (1) high emission efficiency and power efficiency, (2) a low driving voltage, and, in particular, (3) a long life by the use of the aryldiamine compound in combination with various materials excellent in hole injecting properties, hole transporting properties, electron injecting properties, electron transporting properties, electron blocking properties, stability in thin film form, and durability in such a manner as to make these materials exhibit their respective characteristics effectively.

Solution to Problem

With the view of accomplishing the above objects, the inventors noted that aryldiamine compounds with a specific structure is excellent in hole injection, hole transport, stability in thin film form, and durability. They have designed and synthesized a variety of aryldiamine compounds and evaluated their characteristics intensively. As a result, they have found an aryldiamine compound having an aryl group at a specific position to be excellent in hole transporting properties and stability in thin film form, and heat resistance.

The inventors have also made various organic EL devices using the aryldiamine compound and evaluated the characteristics of the devices intensively and, as a result, completed the invention.

The invention provides an aryldiamine compound represented by formula (1):

[Chem. 2]

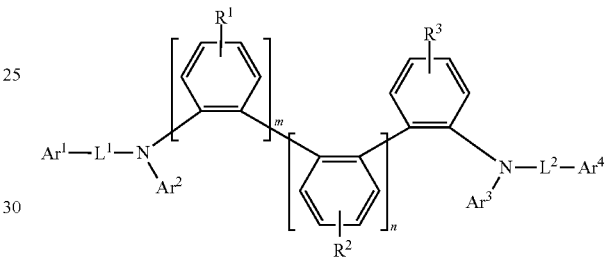

(1)

wherein m and n each represent 0 or 1;
$Ar^1$, $Ar^2$, $Ar^3$, and $Ar^4$ each represent an aromatic hydrocarbon group or an aromatic heterocyclic group;
when m+n is 0 or 1, and $Ar^2$ is an unsubstituted phenyl group, neither $Ar^3$ nor $Ar^4$ is an unsubstituted phenyl group;
$L^1$ and $L^2$ each represent a single bond, a divalent aromatic hydrocarbon group, or a divalent aromatic heterocyclic group; and
$R^1$, $R^2$, and $R^3$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

Preferred embodiments of the aryldiamine compound of the invention are as follows.

(1) A compound wherein m and n are both zero which is represented by formula (1-1a):

[Chem. 3]

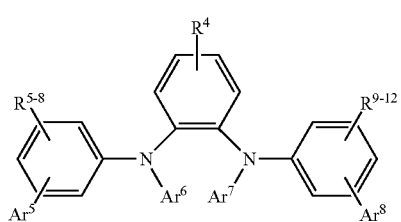

(1-1a)

wherein $Ar^5$ and $Ar^8$ each represent an aromatic hydrocarbon group or an aromatic heterocyclic group;

$Ar^6$ and $Ar^7$ correspond to $Ar^2$ and $Ar^3$ in formula (1), respectively;

when $Ar^6$ is an unsubstituted phenyl group, $Ar^7$ is not an unsubstituted phenyl group;

$R^4$ corresponds to $R^3$ in formula (1);

$R^{5-8}$ represents multiple groups $R^5$, $R^6$, $R^7$, and $R^8$ bonded to the benzene ring at different positions;

$R^{9-12}$ represents multiple groups $R^9$, $R^{10}$, $R^{11}$, and $R^{12}$ bonded to the benzene ring at different positions; and $R^5$, $R^6$, $R^7$, $R^8$, $R^9$, $R^{10}$, $R^{11}$, and $R^{12}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

(2) A compound wherein m and n are both zero which is represented by formula (1-1b):

[Chem. 4]

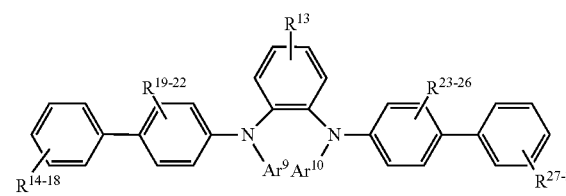

(1-1b)

wherein $Ar^9$ and $Ar^{10}$ correspond to $Ar^2$ and $Ar^3$ in formula (1), respectively;

when $Ar^9$ is an unsubstituted phenyl group, $Ar^{10}$ is not an unsubstituted phenyl group;

$R^{13}$ corresponds to $R^3$ in formula (1);

$R^{14-18}$ represents multiple groups $R^{14}$, $R^{15}$, $R^{16}$, $R^{17}$, and $R^{18}$ bonded to the benzene ring at different positions;

$R^{19-22}$ represents multiple groups $R^{19}$, $R^{20}$, $R^{21}$, and $R^{22}$ bonded to the benzene ring at different positions;

$R^{23-26}$ represents multiple groups $R^{23}$, $R^{24}$, $R^{25}$, and $R^{26}$ bonded to the benzene ring at different positions;

$R^{27-31}$ represents multiple groups $R^{27}$, $R^{28}$, $R^{29}$, $R^{30}$, and $R^{31}$ bonded to the benzene ring at different positions; and $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{30}$, and $R^{31}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

(3) A compound wherein m=1 and n=0 which is represented by formula (1-2a):

[Chem. 5]

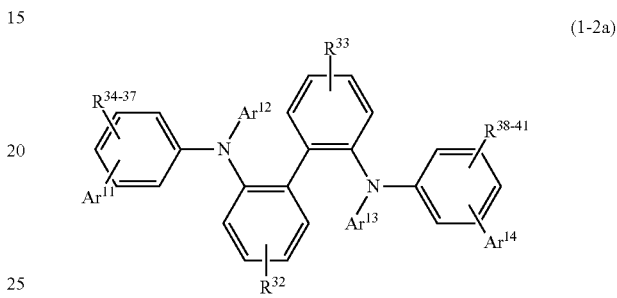

(1-2a)

wherein $Ar^{11}$ and $Ar^{14}$ each represent an aromatic hydrocarbon group or an aromatic heterocyclic group;

$Ar^{12}$ and $Ar^{13}$ correspond to $Ar^2$ and $Ar^3$ in formula (1), respectively;

when $Ar^{12}$ is an unsubstituted phenyl group, $Ar^{13}$ is not an unsubstituted phenyl group;

$R^{32}$ corresponds to $R^1$ in formula (1);

$R^{33}$ corresponds to $R^3$ in formula (1);

$R^{34-37}$ represents multiple groups $R^{34}$, $R^{35}$, $R^{36}$, and $R^{37}$ bonded to the benzene ring at different positions;

$R^{38-41}$ represents multiple groups $R^{38}$, $R^{39}$, $R^{40}$, and $R^{41}$ bonded to the benzene ring at different positions; and $R^{34}$, $R^{35}$, $R^{36}$, $R^{37}$, $R^{38}$, $R^{39}$, $R^{40}$, and $R^{41}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

(4) A compound wherein m=1 and n=0 which is represented by formula (1-2b):

[Chem.6]

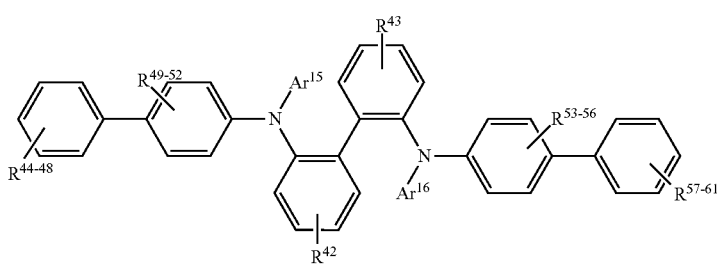

(1-2b)

wherein $Ar^{15}$ and $Ar^{16}$ correspond to $Ar^2$ and $Ar^3$ in formula (1), respectively;

when $Ar^{15}$ is an unsubstituted phenyl group, $Ar^{16}$ is not an unsubstituted phenyl group;

$R^{42}$ corresponds to $R^1$ in formula (1);

$R^{43}$ corresponds to $R^3$ in formula (1);

$R^{44-48}$ represents multiple groups $R^{44}$, $R^{45}$, $R^{46}$, $R^{47}$, and $R^{48}$ bonded to the benzene ring at different positions;

$R^{49-52}$ represents multiple groups $R^{49}$, $R^{50}$, $R^{51}$, and $R^{52}$ bonded to the benzene ring at different positions;

$R^{53-56}$ represents multiple groups $R^{53}$, $R^{54}$, $R^{55}$, and $R^{56}$ bonded to the benzene ring at different positions;

$R^{57-61}$ represents multiple groups $R^{57}$, $R^{58}$, $R^{59}$, $R^{60}$, and $R^{61}$ bonded to the benzene ring at different positions; and $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, and $R^{61}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

(5) A compound wherein m and n are both one which is represented by formula (1-3a):

[Chem. 7]

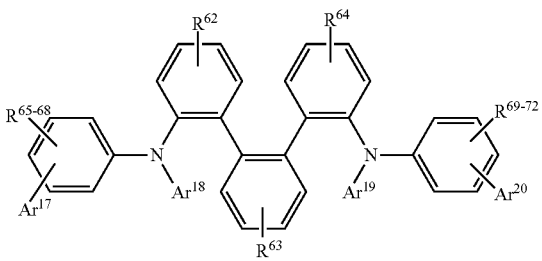

(1-3a)

wherein $Ar^{17}$ and $Ar^{20}$ each represent an aromatic hydrocarbon group or an aromatic heterocyclic group;

$Ar^{18}$ and $Ar^{19}$ correspond to $Ar^2$ and $Ar^3$ in formula (1), respectively;

$R^{62}$ and $R^{63}$ correspond to $R^1$ and $R^2$ in formula (1), respectively;

$R^{64}$ corresponds to $R^3$ in formula (1);

$R^{65-68}$ represents multiple groups $R^{65}$, $R^{66}$, $R^{67}$, and $R^{68}$ bonded to the benzene ring at different positions;

$R^{69-72}$ represent multiple groups $R^{69}$, $R^{70}$, $R^{71}$, and $R^{72}$ bonded to the benzene ring at different positions; and $R^{65}$, $R^{66}$, $R^{67}$, $R^{68}$, $R^{69}$, $R^{70}$, $R^{71}$, and $R^{72}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

(6) A compound wherein m and n are both one which is represented by formula (1-3b):

[Chem. 8]

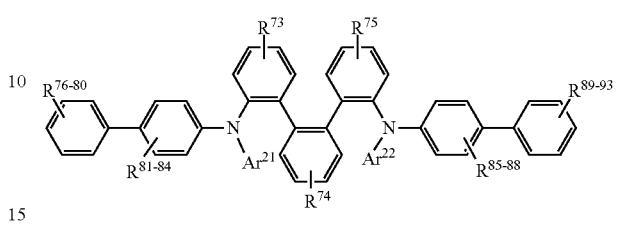

(1-3b)

wherein $Ar^{21}$ and $Ar^{22}$ correspond to $Ar^2$ and $Ar^3$ in formula (1), respectively;

$R^{73}$ and $R^{74}$ correspond to $R^1$ and $R^2$ in formula (1), respectively;

$R^{75}$ corresponds to $R^3$ in formula (1);

$R^{76-80}$ represents multiple groups $R^{76}$, $R^{77}$, $R^{78}$, $R^{79}$, and $R^{80}$ bonded to the benzene ring at different positions;

$R^{81-84}$ represents multiple groups $R^{81}$, $R^{82}$, $R^{83}$, and $R^{84}$ bonded to the benzene ring at different positions;

$R^{85-88}$ represents multiple groups $R^{85}$, $R^{86}$, $R^{87}$, and $R^{88}$ bonded to the benzene ring at different positions;

$R^{89-93}$ represents multiple groups $R^{89}$, $R^{90}$, $R^{91}$, $R^{92}$, and $R^{93}$ bonded to the benzene ring at different positions; and $R^{76}$, $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, and $R^{93}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

In the description of the invention, the aromatic hydrocarbon group, aromatic heterocyclic group, divalent aromatic hydrocarbon group, divalent aromatic heterocyclic group, alkyl group having 1 to 6 carbon atoms, cycloalkyl group having 5 to 10 carbon atoms, alkenyl group having 2 to 6 carbon atoms, alkoxy group having 1 to 6 carbon atoms, cycloalkoxy group having 5 to 10 carbon atoms, and aryloxy group as represented by $Ar^1$ to $Ar^{22}$, $L^1$, $L^2$, and $R^1$ to $R^{93}$ may be substituted or unsubstituted unless otherwise specified.

Two or more of $Ar^1$ to $Ar^{22}$, both of $L^1$ and $L^2$, or two or more of $R^1$ to $R^{93}$ which are present in the same molecule, may have the same or different structures.

The aliphatic hydrocarbon groups, such as alkyl, alkenyl, and alkoxy groups, may be either straight or branched unless otherwise noted. The aromatic hydrocarbon group and aromatic heterocyclic group may be monocyclic or polycyclic or may have a fused polycyclic structure unless otherwise defined. Similarly, the divalent aromatic hydrocarbon group or aromatic heterocyclic group may be either monocyclic or polycyclic and may have a fused polycyclic structure unless otherwise specified.

The invention also provides an organic electroluminescent device comprising a pair of electrodes and at least one organic layer disposed between the pair of electrodes, wherein the aryldiamine compound of the invention is used as comprising material of the at least one organic layer.

In preferred embodiments of the organic EL device of the invention, (a) the organic layer is a hole transport layer, (b)

the organic layer is an electron blocking layer, (c) the organic layer is a hole injection layer, (d) the organic layer is an emitting layer, and/or (e) the hole transport layer has a dual layer structure composed of a first hole transport layer and a second hole transport layer.

Advantageous Effects of Invention

The aryldiamine compound of the invention is a novel compound and has (1) high hole injecting properties, (2) large hole mobility, (3) excellent electron blocking properties, (4) stability in thin film form, and (5) high heat resistance.

The organic EL device of the invention exhibits (6) high emission efficiency, (7) high power efficiency, (8) low onset voltage, (9) low driving voltage, and (10) long life.

The aryldiamine compound of the invention is suitably used as a material forming a hole transport layer or a hole injection layer of an organic EL device because of its higher hole injecting properties, higher hole mobility, higher electron blocking properties, and higher stability to electrons compared with conventional materials. An organic EL device having a hole transport layer or injection layer formed of the aryldiamine compound of the invention is capable of confining the generated excitons in the emitting layer, thereby providing an increased probability of hole-electron recombination to achieve high emission efficiency, and, at the same time, it drives at a lower voltage and has improved durability.

The aryldiamine compound of the invention is also suited for use as a material forming an electron blocking layer of an organic EL device because of its higher electron blocking ability, higher hole transporting properties, and higher stability in thin film form as compared with conventional materials. An organic EL device having an electron blocking layer formed of the aryldiamine compound of the invention achieves high emission efficiency, a low driving voltage, high current resistance, and a high maximum luminance.

The aryldiamine compound of the invention is also suitable as a material forming an emission layer of an organic EL device. The aryldiamine compound has higher hole transporting properties and a wider band gap than conventional materials. Therefore, the aryldiamine compound can be used as a host material which is doped with a fluorescent or phosphorescent guest material called a dopant to form an emission layer. An organic EL device having such an emission layer drives at a low voltage and achieves improved emission efficiency.

As described, the aryldiamine compound of the invention is useful as a material forming the hole injection layer, hole transport layer, electron blocking layer, or emission layer of an organic EL device, exhibiting large hole mobility, excellent electron blocking ability, stability in thin film form, and high heat resistance. The organic EL device of the invention has high emission efficiency and high power efficiency and, therefore, realizes reductions in driving voltage and onset voltage. It also enjoys high durability and long service life.

DESCRIPTION OF EMBODIMENTS

[I] Aryldiamine Compounds

Figure 1:
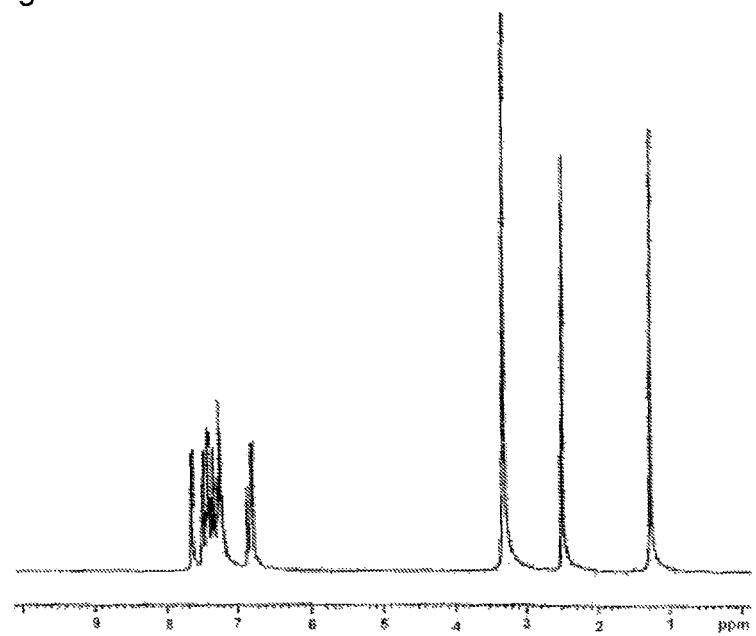
FIG. 1 is a $^1$H-NMR spectrum of Compound 1-2 of Example 1.
Figure 2:
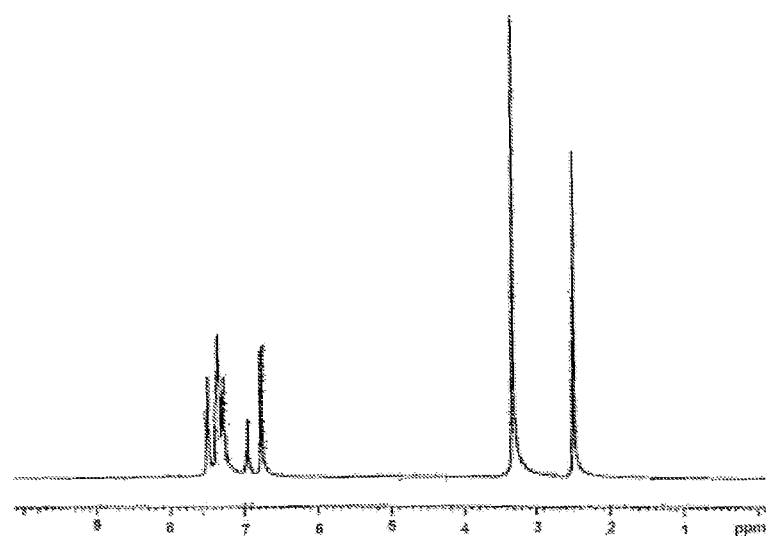
FIG. 2 is a $^1$H-NMR spectrum of Compound 2-1 of Example 2.
Figure 3:
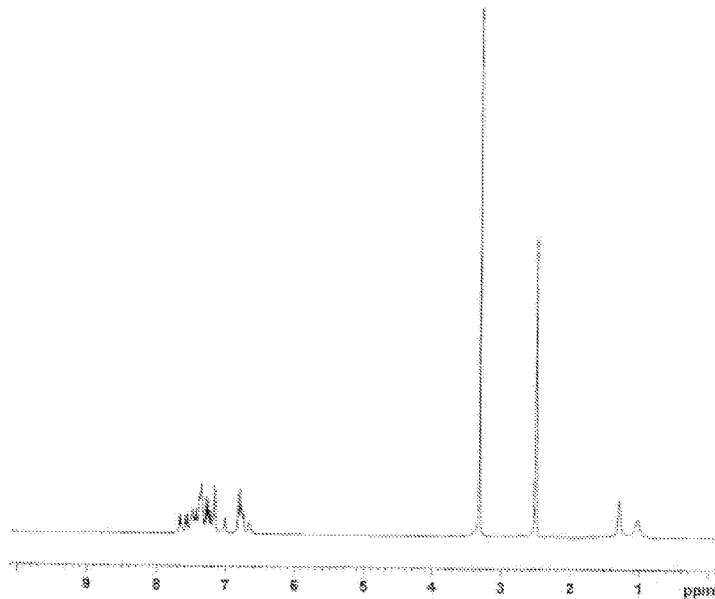
FIG. 3 is a $^1$H-NMR spectrum of Compound 2-4 of Example 3.

The invention provides a novel aryldiamine compound which has two amino groups linked via a specific phenylene, biphenylene, or triphenylene group and which is represented by formula (1):

[Chem. 9]

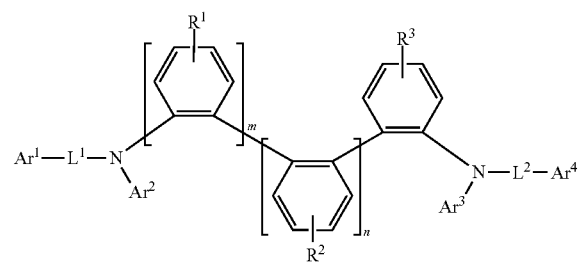

(1)

The aryldiamine compound of formula (1) include three embodiments: a compound represented by formula (1-1a) below, a compound represented by formula (1-2a) below, and a compound represented by formula (1-3a) below. Each embodiment is specified by the m and n values and $L^1$, $L^2$, $Ar^1$, and $Ar^4$ definitions in formula (1).

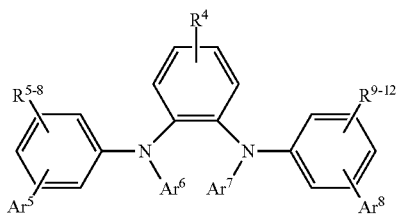

(1-1a)

The compound represented by formula (1-1a) is an embodiment of formula (1), in which m is 0, n is 0, $L^1$ is a single bond, $L^2$ is a single bond, $Ar^1$ is a phenyl group substituted by $Ar^5$ and $R^{5-8}$, and $Ar^4$ is a phenyl group substituted by $Ar^8$ and $R^{9-12}$.

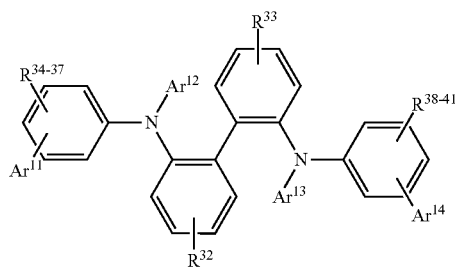

(1-2a)

The compound represented by formula (1-2a) is an embodiment of formula (1), in which m is 1, n is 0, $L^1$ is a single bond, $L^2$ is a single bond, $Ar^1$ is a phenyl group substituted by $Ar^{11}$ and $R^{34-37}$, and $Ar^4$ is a phenyl group substituted by $Ar^{14}$ and $R^{38-41}$.

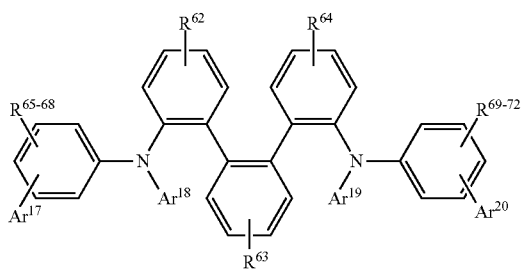

(1-3a)

The compound represented by formula (1-3a) is an embodiment of formula (1), in which m is 1, n is 1, $L^1$ is a single bond, $L^2$ is a single bond, $Ar^1$ is a phenyl group substituted by $Ar^{17}$ and $R^{65-68}$, and $Ar^4$ is a phenyl group substituted by $Ar^{20}$ and $R^{69-72}$.

$Ar^6$ and $Ar^7$ in formula (1-1a) correspond to $Ar^2$ and $Ar^3$ in formula (1), respectively.

$Ar^{12}$ and $Ar^{13}$ in formula (1-2a) correspond to $Ar^2$ and $Ar^3$ in formula (1), respectively.

$Ar^{18}$ and $Ar^{19}$ in formula (1-3a) correspond to $Ar^2$ and $Ar^3$ in formula (1), respectively.

$R^4$ in formula (1-1a) corresponds to $R^3$ in formula (1).

$R^{32}$ in formula (1-2a) corresponds to $R^1$ in formula (1).

$R^{33}$ in formula (1-2a) corresponds to $R^3$ in formula (1).

$R^{62}$ and $R^{63}$ in formula (1-3a) correspond to $R^1$ and $R^2$ in formula (1), respectively.

$R^{64}$ in formula (1-3a) corresponds to $R^3$ in formula (1).

In formula (1-1a), $R^{5-8}$ represents multiple groups $R^5$, $R^6$, $R^7$, and $R^8$ bonded to the benzene ring at different positions, and $R^{9-12}$ represents multiple groups $R^9$, $R^{10}$, $R^{11}$, and $R^{12}$ bonded to the benzene ring at different positions.

In formula (1-2a), $R^{34-37}$ represents multiple groups $R^{34}$, $R^{35}$, $R^{36}$, and $R^{37}$ bonded to the benzene ring at different positions, and $R^{38-41}$ represents multiple groups $R^{38}$, $R^{39}$, $R^{40}$, and $R^{41}$ bonded to the benzene ring at different positions.

In formula (1-3a), $R^{65-68}$ represents multiple groups $R^{65}$, $R^{66}$, $R^{67}$, and $R^{68}$ bonded to the benzene ring at different positions, and $R^{69-72}$ represents multiple groups $R^{69}$, $R^{70}$, $R^{71}$, and $R^{72}$ bonded to the benzene ring at different positions.

The aryldiamine compounds of formulae (1-1a), (1-2a), and (1-3a) include three embodiments: a compound represented by formula (1-1b) below, a compound represented by formula (1-2b) below, and a compound represented by formula (1-3b) below, respectively. Each embodiment is specified by the structures of $Ar^1$ and $Ar^4$ in formula (1).

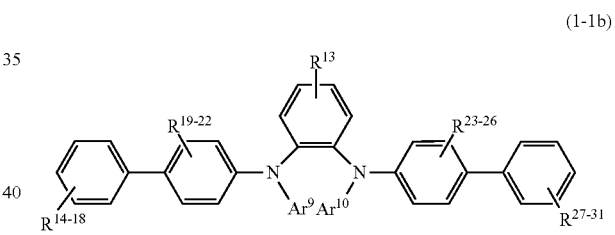

(1-1b)

The compound represented by formula (1-1b) is an embodiment of formula (1), in which $Ar^1$ is a biphenylyl group substituted by $R^{14-18}$ and $R^{19-22}$, and $Ar^4$ is a biphenylyl group substituted by $R^{23-26}$ and $R^{27-31}$.

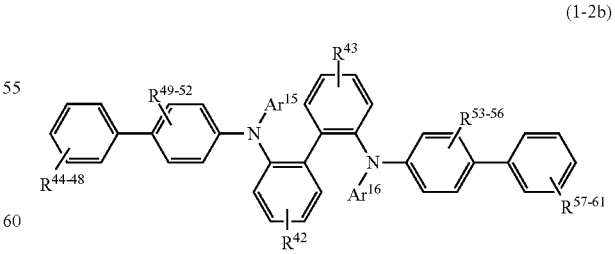

(1-2b)

The compound represented by formula (1-2b) is an embodiment of formula (1), in which $Ar^1$ is a biphenylyl group substituted by $R^{44-48}$ and $R^{49-52}$, and $Ar^4$ is a biphenylyl group substituted by $R^{53-56}$ and $R^{57-61}$.

[Chem. 15]

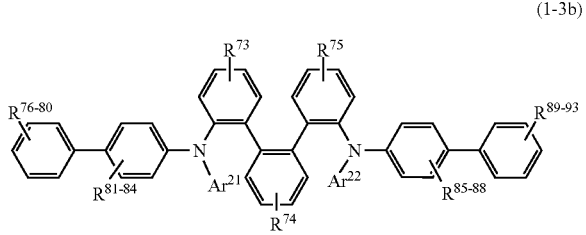

(1-3b)

The compound represented by formula (1-3b) is an embodiment of formula (1), in which $Ar^1$ is a biphenylyl group substituted by $R^{76-80}$ and $R^{81-84}$, and $Ar^4$ is a biphenylyl group substituted by $R^{85-88}$ and $R^{89-93}$.

$Ar^9$ and $Ar^{10}$ in formula (1-1b) correspond to $Ar^2$ and $Ar^3$ in formula (1), respectively, and to $Ar^6$ and $Ar^7$ in formula (1-1a), respectively.

$Ar^{15}$ and $Ar^{16}$ in formula (1-2b) correspond to $Ar^2$ and $Ar^3$ in formula (1), respectively, and to $Ar^{12}$ and $Ar^{13}$ in formula (1-2a), respectively.

$Ar^{21}$ and $Ar^{22}$ in formula (1-3b) correspond to $Ar^2$ and $Ar^3$ in formula (1), respectively, and to $Ar^{18}$ and $Ar^{19}$ in formula (1-3a), respectively.

$R^{13}$ in formula (1-1b) corresponds to $R^3$ in formula (1) and $R^4$ in formula (1-1a).

$R^{42}$ in formula (1-2b) corresponds to $R^1$ in formula (1) and $R^{32}$ in formula (1-2a).

$R^{43}$ in formula (1-2b) corresponds to $R^3$ in formula (1) and $R^{33}$ in formula (1-2a).

$R^{73}$ and $R^{74}$ in formula (1-3b) correspond to $R^1$ and $R^2$ in formula (1), respectively, and to $R^{62}$ and $R^{63}$ in formula (1-3a), respectively.

$R^{75}$ in formula (1-3b) corresponds to $R^3$ in formula (1) and $R^{64}$ in formula (1-3a).

In formula (1-1b), $R^{14-18}$ represents multiple groups $R^{14}$, $R^{15}$, $R^{16}$, $R^{17}$, and $R^{18}$ bonded to the benzene ring at different positions; $R^{19-22}$ represents multiple groups $R^{19}$, $R^{20}$, $R^{21}$, and $R^{22}$ bonded to the benzene ring at different positions; $R^{23-26}$ represents multiple groups $R^{23}$, $R^{24}$, $R^{25}$, and $R^{26}$ bonded to the benzene ring at different positions; and $R^{27-31}$ represents multiple groups $R^{27}$, $R^{28}$, $R^{29}$, $R^{30}$, and $R^{31}$ bonded to the benzene ring at different positions.

In formula (1-2b), $R^{44-48}$ represents multiple groups $R^{44}$, $R^{45}$, $R^{46}$, $R^{47}$, and $R^{48}$ bonded to the benzene ring at different positions; $R^{49-52}$ represents multiple groups $R^{49}$, $R^{50}$, $R^{51}$, and $R^{52}$ bonded to the benzene ring at different positions; $R^{53-56}$ represents multiple groups $R^{53}$, $R^{54}$, $R^{55}$, and $R^{56}$ bonded to the benzene ring at different positions; and $R^{57-61}$ represents multiple groups $R^{57}$, $R^{58}$, $R^{59}$, $R^{60}$, and $R^{61}$ bonded to the benzene ring at different positions.

In formula (1-3b), $R^{76-80}$ represents multiple groups $R^{76}$, $R^{77}$, $R^{78}$, $R^{79}$, and $R^{80}$ bonded to the benzene ring at different positions; $R^{81-84}$ represents multiple groups $R^{81}$, $R^{82}$, $R^{83}$, and $R^{84}$, $R^{85-88}$ represents multiple groups $R^{85}$, $R^{86}$, $R^{87}$, and $R^{88}$ bonded to the benzene ring at different positions; and $R^{89-93}$ represents multiple groups $R^{89}$, $R^{90}$, $R^{91}$, $R^{92}$, and $R^{93}$ bonded to the benzene ring at different positions.

(m, n)

m and n each represent an integer 0 or 1.

($Ar^1$ to $Ar^{22}$)

$A^1$ through $Ar^{22}$ each represent an aromatic hydrocarbon group or an aromatic heterocyclic group.

Note that, when in formula (1) $Ar^2$ is an unsubstituted phenyl group, and m+n=0 or 1, neither $Ar^3$ nor $Ar^4$ is an unsubstituted phenyl group.

Accordingly, in formula (1-1a), when $Ar^6$ is an unsubstituted phenyl group, $Ar^7$ is not an unsubstituted phenyl group. In formula (1-1b), when $Ar^9$ is an unsubstituted phenyl group, $Ar^{10}$ is not an unsubstituted phenyl group.

Similarly, in formula (1-2a), when $Ar^{12}$ is an unsubstituted phenyl group, $Ar^{13}$ is not an unsubstituted phenyl group. In formula (1-2b), when $Ar^{15}$ is an unsubstituted phenyl group, $Ar^{16}$ is not an unsubstituted phenyl group.

Examples of the aromatic hydrocarbon group or aromatic heterocyclic group as represented by $Ar^1$ through $Ar^{22}$ include aryl groups having 6 to 30 carbon atoms and heteroaryl groups having 2 to 20 carbon atoms, such as phenyl, biphenylyl, terphenylyl, naphthyl, anthracenyl, phenanthrenyl, fluorenyl, spirobifluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, naphthylidinyl, acridinyl, and carbolinyl.

The aromatic hydrocarbon group or aromatic heterocyclic group represented by $Ar^1$ to $Ar^{22}$ may optionally be substituted. Examples of substituents include a deuterium atom, a cyano group, a nitro group, and, in addition, the following atoms and groups:

Halogen atoms, such as fluorine, chlorine, bromine, and iodine; alkyl groups having 1 to 6 carbon atoms, such as methyl, ethyl, n-propyl, isopropyl, n-butyl, isobutyl, tert-butyl, n-pentyl, isopentyl, neopentyl, and n-hexyl; alkoxy groups having 1 to 6 carbon atoms, such as methoxy, ethoxy, and propoxy; alkenyl groups, such as vinyl and allyl; aryloxy groups, such as phenoxy and tolyloxy; arylalkoxy groups, such as benzoyloxy and phenethyloxy; aromatic hydrocarbon groups, such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups, such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, and carbolinyl; arylvinyl groups, such as styryl and naphthylvinyl; and acyl groups, such as acetyl and benzoyl.

These substituents may be independent of one another or may be connected via a single bond, a substituted or unsubstituted methylene group, an oxygen atom, or a sulfur atom to form a ring.

$L^1$ and $L^2$ each represent a single bond, a divalent aromatic hydrocarbon group, or a divalent aromatic heterocyclic group.

The divalent aromatic hydrocarbon group or divalent aromatic heterocyclic group as represented by $L^1$ and $L^2$ is a divalent group derived by removing two hydrogen atoms from an aromatic hydrocarbon or an aromatic heterocyclic ring, respectively.

Examples of the aromatic hydrocarbons and aromatic heterocyclic rings from which $L^1$ and $L^2$ are derived include benzene, biphenyl, terphenyl, naphthalene, anthracene, phenanthrene, fluorene, spirobifluorene, indane, pyrene, perylene, fluoranthene, triphenylene, pyridine, pyrimidine, triazine, furan, pyrrole, thiophene, quinoline, isoquinoline, benzofuran, benzothiophene, indoline, carbazole, benzoxazole, benzothiazole, quinoxaline, benzimidazole, pyrazole, dibenzofuran, dibenzothiophene, naphthyridine, and acridine.

The divalent aromatic hydrocarbon group or divalent aromatic heterocyclic group as represented by $L^1$ and $L^2$ may optionally be substituted. Examples of substituents include those recited above as substituents on the aromatic hydrocarbon group or aromatic heterocyclic group represented by $Ar^1$ to $Ar^{22}$. Embodiments that the substituents on $L^1$ and $L^2$ may have are the same as the embodiments the substituents on $Ar^1$ to $Ar^{22}$ may have.

($R^1$ through $R^{93}$)

$R^1$ through $R^{93}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

Examples of the alkyl groups having 1 to 6 carbon atoms, cycloalkyl groups having 5 to 10 carbon atoms, and alkenyl groups having 2 to 6 carbon atoms as $R^1$ to $R^{93}$ include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl.

Examples of the alkoxy groups having 1 to 6 carbon atoms and cycloalkoxy groups having 5 to 10 carbon atoms as $R^1$ to $R^{93}$ include methoxy, ethoxy, n-propoxy, isopropoxy, n-butoxy, tert-butoxy, n-pentyloxy, n-hexyloxy, cyclopentyloxy, cyclohexyloxy, cycloheptyloxy, cyclooctyloxy, 1-adamantyloxy, and 2-adamantyloxy.

Examples of the aromatic hydrocarbon group or aromatic heterocyclic group as $R^1$ to $R^{93}$ include those enumerated above as examples of $Ar^1$ to $Ar^{22}$.

Examples of the aryloxy group as $R^1$ to $R^{93}$ include phenoxy, biphenylyloxy, terphenylyloxy, naphthyloxy, anthracenyloxy, phenanthrenyloxy, fluorenyloxy, indenyloxy, pyrenyloxy, and perylenyloxy.

The alkyl groups having 1 to 6 carbon atoms, cycloalkyl groups having 5 to 10 carbon atoms, alkenyl groups having 2 to 6 carbon atoms, alkoxy groups having 1 to 6 carbon atoms, cycloalkoxy groups having 5 to 10 carbon atoms, aromatic hydrocarbon group, aromatic heterocyclic group, and aryloxy group as represented by $R^1$ to $R^{93}$ may be optionally substituted. Examples of substituents include those recited above as substituents on the aromatic hydrocarbon groups or aromatic heterocyclic groups represented by $Ar^1$ to $Ar^{22}$. Embodiments that the substituents on $R^1$ to $R^{93}$ may have are the same as the embodiments that the substituents on $A^1$ to $Ar^{22}$ may have.

PREFERRED EMBODIMENTS

Preferred embodiments of the aryldiamine compounds will then be described.

Preferred of the aryldiamine compounds of the invention are those of formulae (1-1a), (1-2a), and (1-3a), and more preferred are those of formulae (1-1b), (1-2b), and (1-3b).

The aryldiamine compounds are preferably symmetric. As used herein, the term "symmetric" means having the following structures.

In the case of the compounds of formula (1-1a), $Ar^6$ and $Ar^7$ have the same structure inclusive of the kind and position of their substituents, and the combination of $Ar^5$ and the phenyl group substituted by $R^{5-8}$ and the combination of $Ar^8$ and the phenyl group substituted by $R^{9-12}$ also have the same structure inclusive of the kind and position of their substituents. The same applies to the formula (1-1b).

In the case of the compounds of formula (1-2a), $Ar^{12}$ and $Ar^{13}$ have the same structure inclusive of the kind and position of their substituents; the combination of $Ar^{11}$ and the phenyl group substituted by $R^{34-37}$ and the combination of $Ar^{14}$ and the phenyl group substituted by $R^{38-41}$ have the same structure inclusive of the kind and position of their substituents; and $R^{32}$ and $R^{33}$ are the same in both kind and position with respect to the amino group on the respective benzene rings to which they are bonded. The same applies to the formula (1-2b).

In the case of the compounds of formula (1-3a), $Ar^{18}$ and $Ar^{19}$ have the same structure inclusive of the kind and position of their substituent; the combination of $Ar^{17}$ and the phenyl group substituted by $R^{65-68}$ and the combination of $Ar^{20}$ and the phenyl group substituted by $R^{69-72}$ have the same structure inclusive of the kind and position of their substituents; and $R^{62}$ and $R^{64}$ are the same in both kind and position with respect to the amino group on the respective benzene rings to which they are bonded. The same applies to the formula (1-3b).

$Ar^2$ and $Ar^3$ are each preferably an aromatic hydrocarbon group, more preferably the one having two or more aromatic rings, such as biphenylyl, terphenylyl, naphthyl, triphenylenyl, spirobifluorenyl, or fluorenyl. The biphenylyl, terphenylyl, triphenylenyl, and spirobifluorenyl groups are preferably unsubstituted. The naphthyl group is preferably unsubstituted or substituted by an aromatic hydrocarbon group, more preferably unsubstituted. The aromatic hydrocarbon group as a substituent on the naphthyl group is preferably selected from phenyl, biphenylyl, and terphenylyl. The fluorenyl group preferably has a substituent. The substituent on the fluorenyl group is preferably methyl or phenyl, more preferably methyl.

$Ar^6$, $Ar^7$, $Ar^9$, and $Ar^{10}$ are each preferably an aromatic hydrocarbon group, more preferably the one having two or more aromatic rings, such as biphenylyl, terphenylyl, naphthyl, triphenylenyl, spirobifluorenyl, or fluorenyl. The biphenylyl, terphenylyl, triphenylenyl, and spirobifluorenyl groups are preferably unsubstituted. The naphthyl group may be substituted. The substituent on the naphthyl group is preferably an aromatic hydrocarbon group, more preferably phenyl, biphenylyl, or terphenylyl. The fluorenyl group preferably has a substituent. The substituent on the fluorenyl group is preferably methyl or phenyl, more preferably methyl.

$Ar^{12}$, $Ar^{13}$, $Ar^{15}$, and $Ar^{16}$ are each preferably an aromatic hydrocarbon group, more preferably the one having two or more aromatic rings, such as biphenylyl, terphenylyl, naphthyl, triphenylenyl, spirobifluorenyl, or fluorenyl. From the viewpoint of heat resistance, in particular, the one having two or more aromatic rings and a fused polycyclic structure, such as triphenylenyl, spirobifluorenyl, or fluorenyl, is preferred. From the viewpoint of emission efficiency and long life, the one having two or more aromatic rings and no fused polycyclic structure, such as biphenylyl or terphenylyl, is preferred. The biphenylyl, terphenylyl, naphthyl, triphenylenyl, and spirobifluorenyl groups are preferably unsubstituted. The fluorenyl group preferably has a substituent. The substituent on the fluorenyl group is preferably methyl or phenyl, more preferably methyl.

$Ar^{18}$, $Ar^9$, $Ar^{21}$, and $Ar^{22}$ are each preferably an aromatic hydrocarbon group, more preferably the one having two or more aromatic rings, such as biphenylyl, terphenylyl, naphthyl, triphenylenyl, spirobifluorenyl, or fluorenyl. The biphenylyl, terphenylyl, naphthyl, triphenylenyl, and spirobifluorenyl groups are preferably unsubstituted. The fluorenyl group preferably has a substituent. The substituent on the fluorenyl group is preferably methyl or phenyl, more preferably methyl.

$Ar^1$ and $Ar^4$ are each preferably an aromatic hydrocarbon group, more preferably the one having no fused polycyclic structure. Specifically, $Ar^1$ and $Ar^4$ are each preferably phenyl, biphenylyl, terphenylyl, triphenylenyl, or fluorenyl, more preferably phenyl, biphenylyl, or terphenylyl, even more preferably biphenylyl. The groups as $Ar^1$ and $Ar^4$ are preferably unsubstituted or substituted by a substituent other than an aromatic heterocyclic group, more preferably unsubstituted. The substituent other than an aromatic heterocyclic group is preferably phenyl, naphthyl, or methyl.

$Ar^5$ and $Ar^8$ are each preferably an aromatic hydrocarbon group, more preferably the one having no fused polycyclic structure, such as phenyl or naphthyl, even more preferably phenyl. The groups as $Ar^5$ and $Ar^8$ are preferably unsubstituted.

$Ar^{11}$ and $Ar^{14}$ are each preferably an aromatic hydrocarbon group, more preferably the one having no fused polycyclic structure. Specifically, $Ar^{11}$ and $Ar^{14}$ are each preferably phenyl, biphenylyl, or naphthyl, more preferably phenyl or biphenylyl, even more preferably phenyl. The groups as $Ar^{11}$ and $Ar^{14}$ are preferably unsubstituted.

$Ar^{17}$ and $Ar^{20}$ are each preferably an aromatic hydrocarbon group, more preferably the one having no fused polycyclic structure, such as phenyl or biphenylyl. The groups as $Ar^{17}$ and $Ar^{20}$ are preferably unsubstituted or substituted by a substituent other than an aromatic heterocyclic group, more preferably unsubstituted.

$L^1$ and $L^2$ are each preferably a single bond.

$R^1$ through $R^4$, $R^{13}$, $R^{32}$, $R^{33}$, $R^{42}$, $R^{43}$, $R^{62}$ through $R^{64}$, and $R^{73}$ through $R^{75}$ are each preferably hydrogen, deuterium, or an aromatic hydrocarbon group, more preferably hydrogen, deuterium, or phenyl, even more preferably hydrogen or deuterium.

$R^5$ through $R^{12}$, $R^{14}$ through $R^{31}$, $R^{34}$ through $R^{41}$, $R^{44}$ through $R^{61}$, $R^{65}$ through $R^{72}$, and $R^{76}$ through $R^{93}$ are each preferably hydrogen, deuterium, or an aromatic hydrocarbon group, more preferably hydrogen, deuterium, or phenyl, even more preferably hydrogen or deuterium.

Specific, but non-limiting, examples of preferred aryldiamine compounds of the invention are shown in FIGS. 5 through 16.

In Compounds 1-1 to 1-32 that are composed of two amino groups linked via a phenylene group, the two substituents each drawn above each one of the nitrogen atoms on the plane of the paper corresponds to -$L^1$-$Ar^1$ and -$L^2$-$Ar^4$ in formula (1), and the two substituents each drawn below each one of the nitrogen atoms correspond to $Ar^2$ and $Ar^3$ in formula (1).

In Compounds 2-1 to 2-36 that are composed of two amino groups linked via a biphenylene group, the substituent below the left (on the paper) nitrogen atom and the substituent above the right nitrogen atom correspond to -$L^1$-$Ar^1$ and -$L^2$-$Ar^4$ in formula (1), and the substituent above the left nitrogen atom and the substituent below the right nitrogen atom correspond to $Ar^2$ and $Ar^3$ in formula (1).

In Compounds 3-1 through 3-14 that are composed of two amino groups linked via a triphenylene group, the two substituents below (on the paper) the nitrogen atoms correspond to -$L^1$-$Ar^1$ and -$L^2$-$Ar^4$ in formula (1), and the two substituents above the nitrogen atoms correspond to $Ar^2$ and $Ar^3$ in formula (1).

Compounds 1-1 to 1-19, 1-21, 1-22, 1-27, and 1-32 belong to formulae (1-1a) and (1-1b), and Compounds 1-25 and 1-26 belong to formula (1-1a).

Compounds 2-1 to 2-5, 2-9 to 2-12, 2-15 to 2-21, 2-23 to 2-26, and 2-28 to 2-31 belong to formulae (1-2a) and (1-2b), and Compounds 2-7, 2-8, and 2-27 belong to formula (1-2a).

Compounds 3-1 and 3-3 to 3-8 belong to formulae (1-3a) and (1-3b), and Compound 3-12 belong to formula (1-3a).

[II] Method of Preparation

The aryldiamine compounds of the invention can be prepared through known processes. For example, the aryldiamine compound may be obtained by cross coupling reaction in the presence of a copper catalyst between a dihalide of a compound having a phenylene, biphenylene or terphenylene structure that is to link the two amino groups of a desired aryldiamine compound and a secondary amine having an aromatic hydrocarbon group or aromatic heterocyclic group bonded to its nitrogen atom.

The crude aryldiamine compound thus prepared can be purified by, for example, column chromatography, adsorption using silica gel, activated carbon, or activated clay, or recrystallization or crystallization from solvents. Purification may also be carried out by sublimation. Identification of the product may be confirmed by NMR analysis. Physical characterization of the aryldiamine compound can be performed by the measurement of melting temperature, glass transition temperature (Tg), work function, and the like.

Melting temperature is a measure of ease of evaporation. The melting point can be measured on a powder sample using a high-sensitivity differential scanning calorimeter (DSC 3100SA, from Bruker AXS).

Glass transition temperature (Tg) is a measure of stability in thin film form. The Tg can be measured in the same manner as for melting temperature.

Work function is a measure of hole transporting or blocking properties. The work function can be measured on a 100 nm-thick film formed on an ITO substrate using an ionization potential measuring device (PYS-202, available from Sumitomo Heavy Industries, Ltd.).

[III] Organic EL Device

The organic EL device basically comprises a spaced pair of electrodes and at least one organic layer disposed therebetween.

Figure 4:
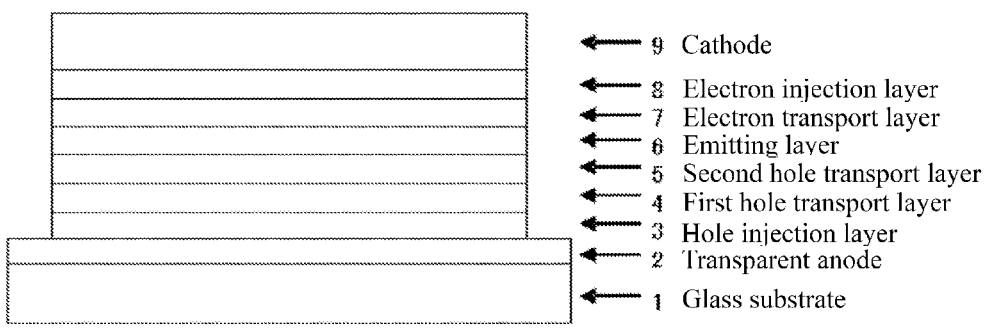
FIG. 4 illustrates the structure of the organic EL devices of Device Examples 1 to 3 and Comparative Device Examples 1 to 4.
Figure 5:
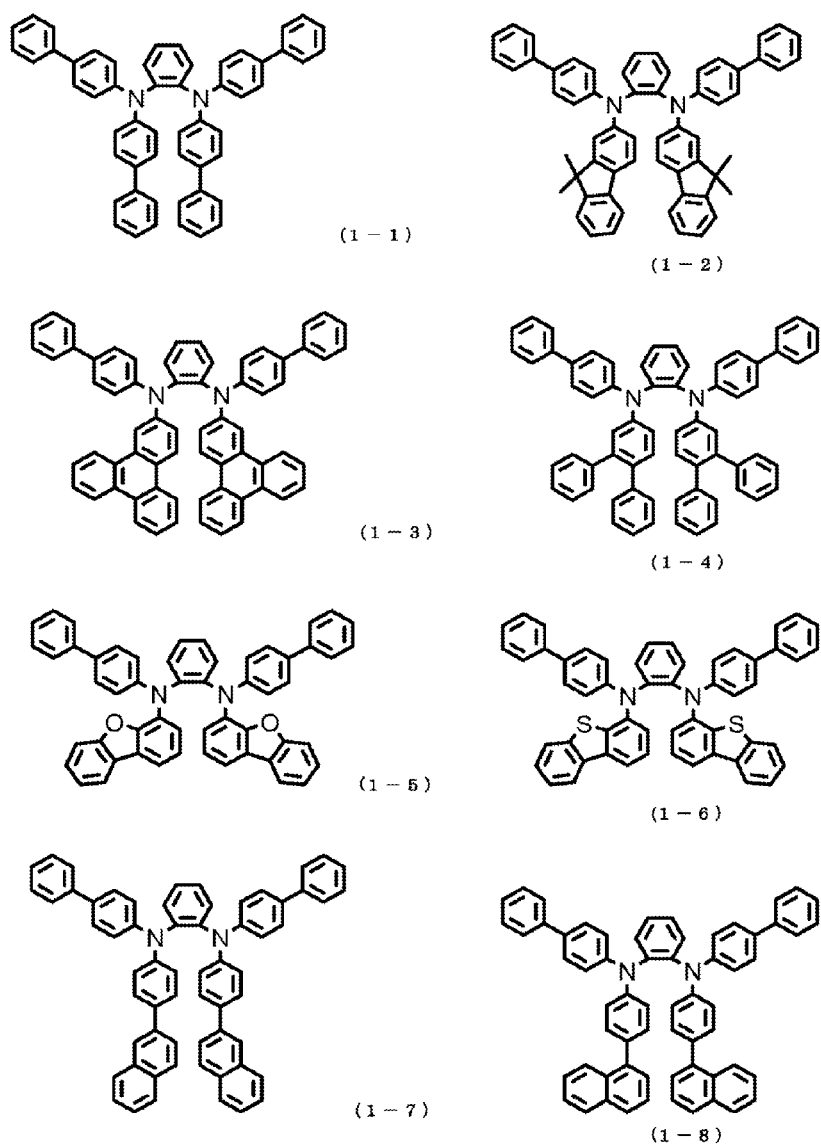
FIG. 5 illustrates structural formulae of Compounds 1-1 through 1-8 which are the aryldiamine compounds.
Figure 6:
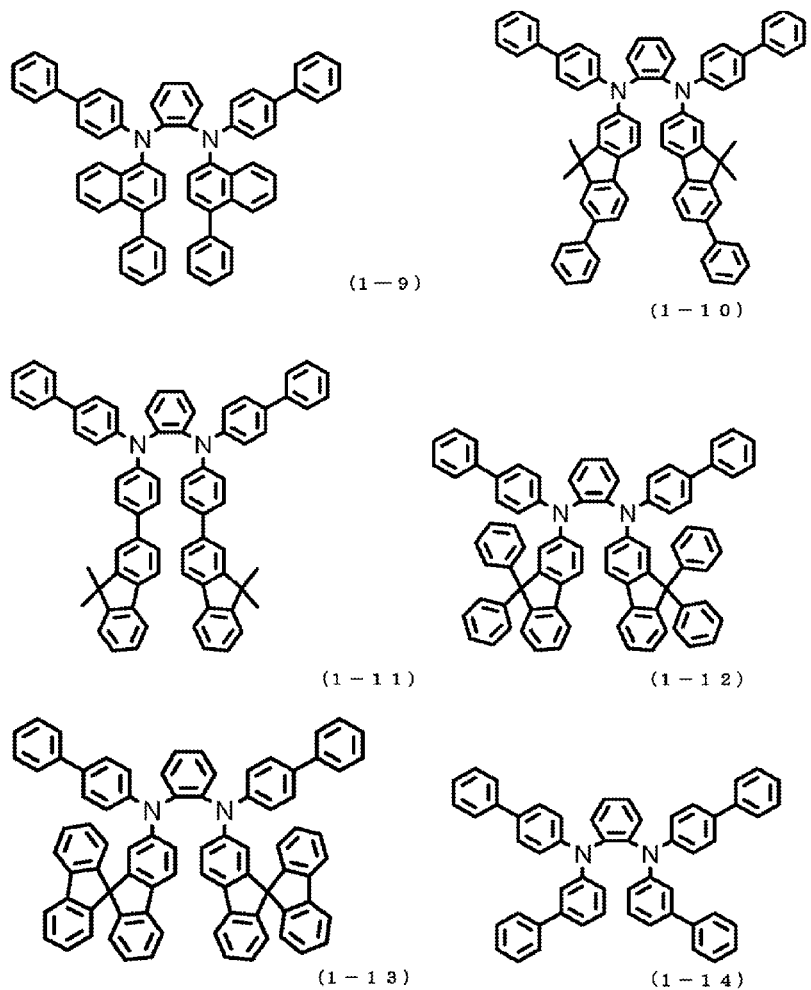
FIG. 6 illustrates structural formulae of Compounds 1-9 through 1-14 which are the aryldiamine compounds.
Figure 7:
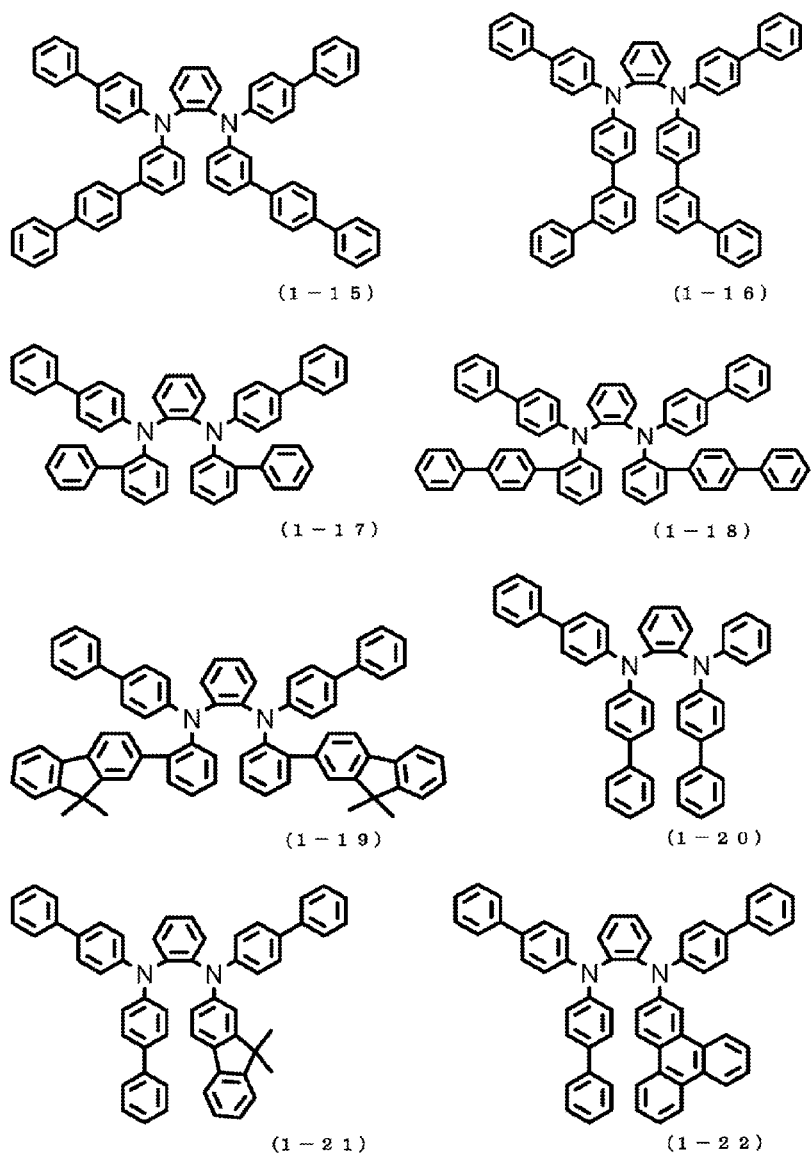
FIG. 7 illustrates structural formulae of Compounds 1-15 through 1-22 which are the aryldiamine compounds.
Figure 8:
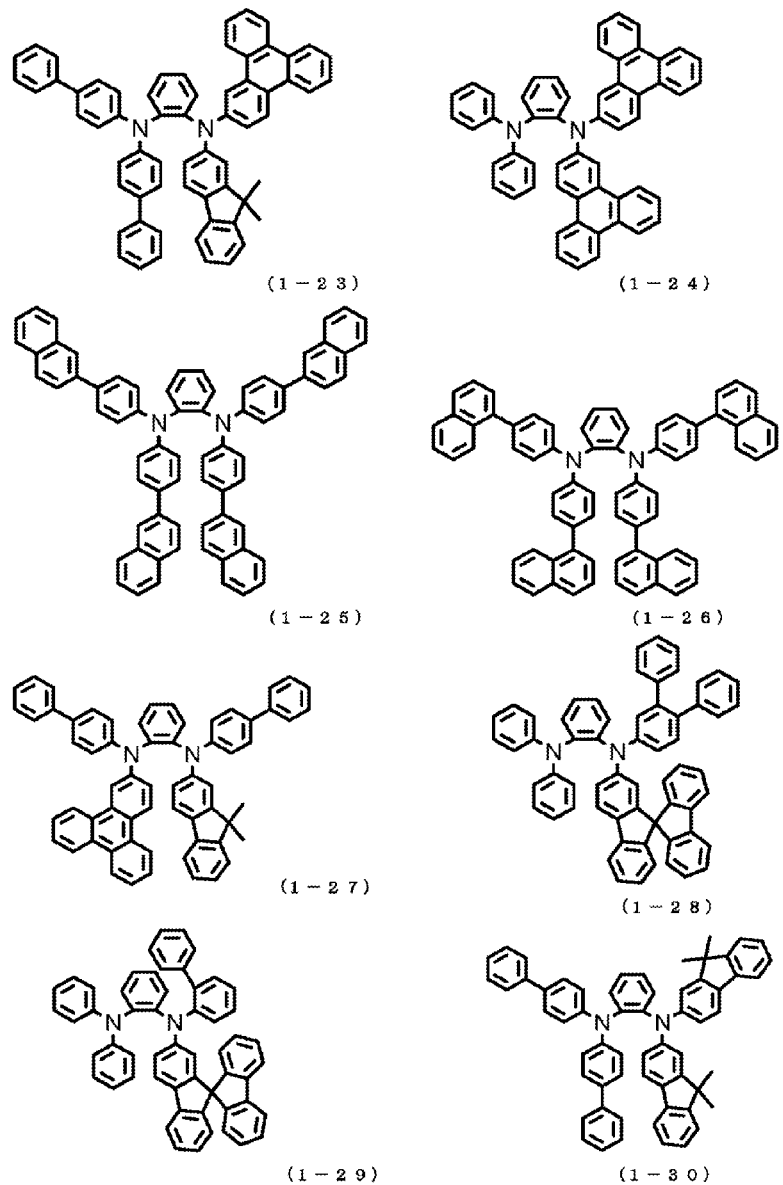
FIG. 8 illustrates structural formulae of Compounds 1-23 through 1-30 which are the aryldiamine compounds.
Figure 9:
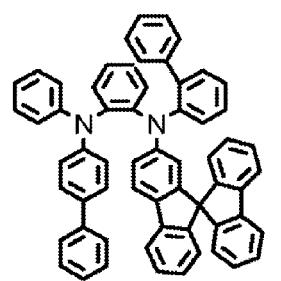
FIG. 9 illustrates structural formulae of Compounds 1-31 and 1-32 which are the aryldiamine compounds.
Figure 9:
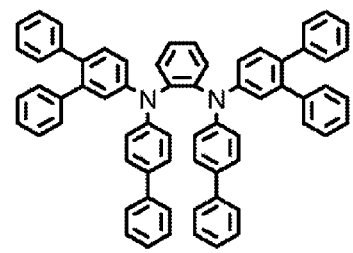
Figure 10:
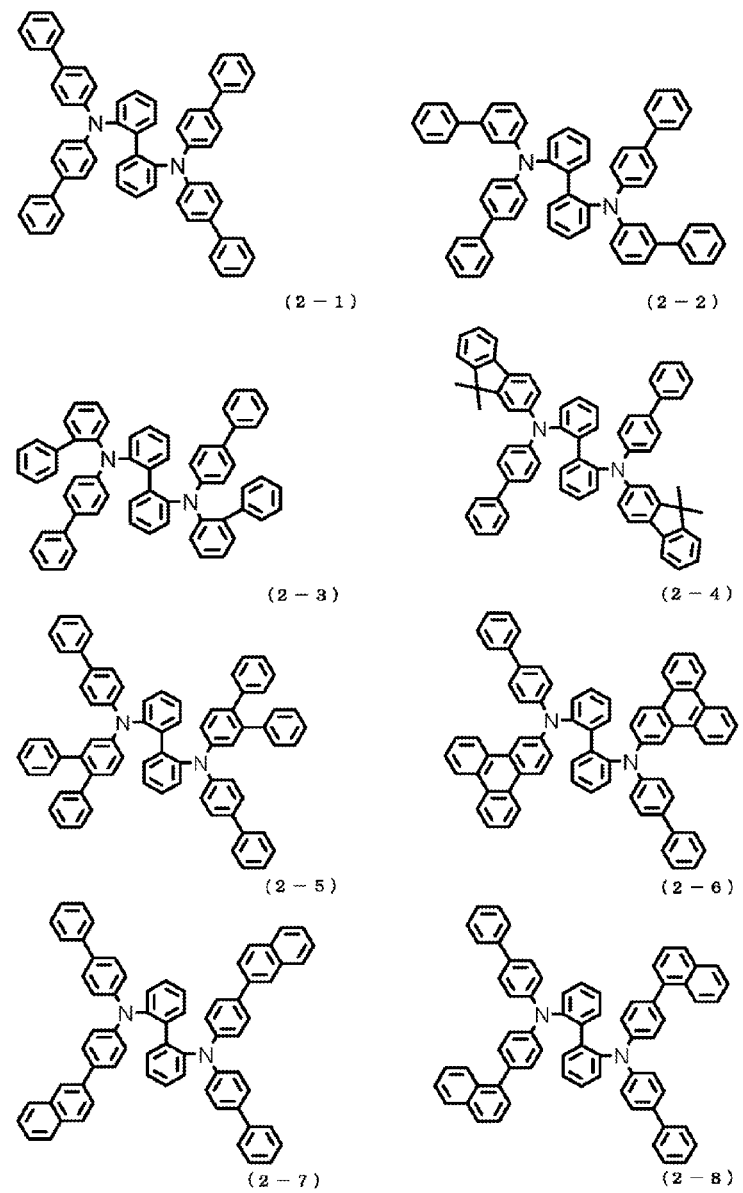
FIG. 10 illustrates structural formulae of Compounds 2-1 through 2-8 which are the aryldiamine compounds.
Figure 11:
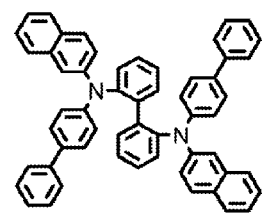
FIG. 11 illustrates structural formulae of Compounds 2-9 through 2-16 which are the aryldiamine compounds.
Figure 11:
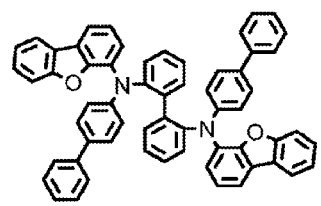
Figure 11:
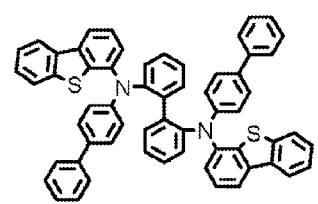
Figure 11:
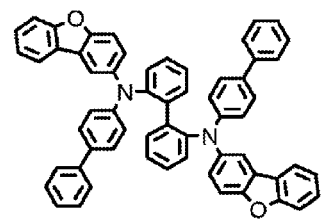
Figure 11:
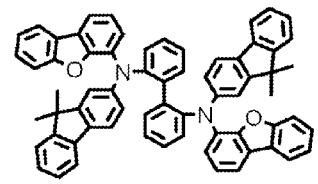
Figure 11:
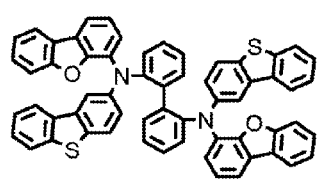
Figure 11:
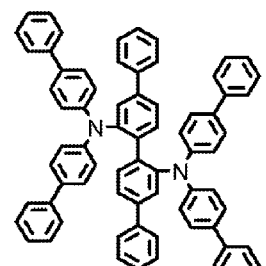
Figure 11:
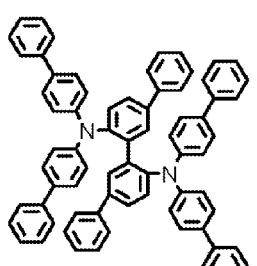
Figure 12:
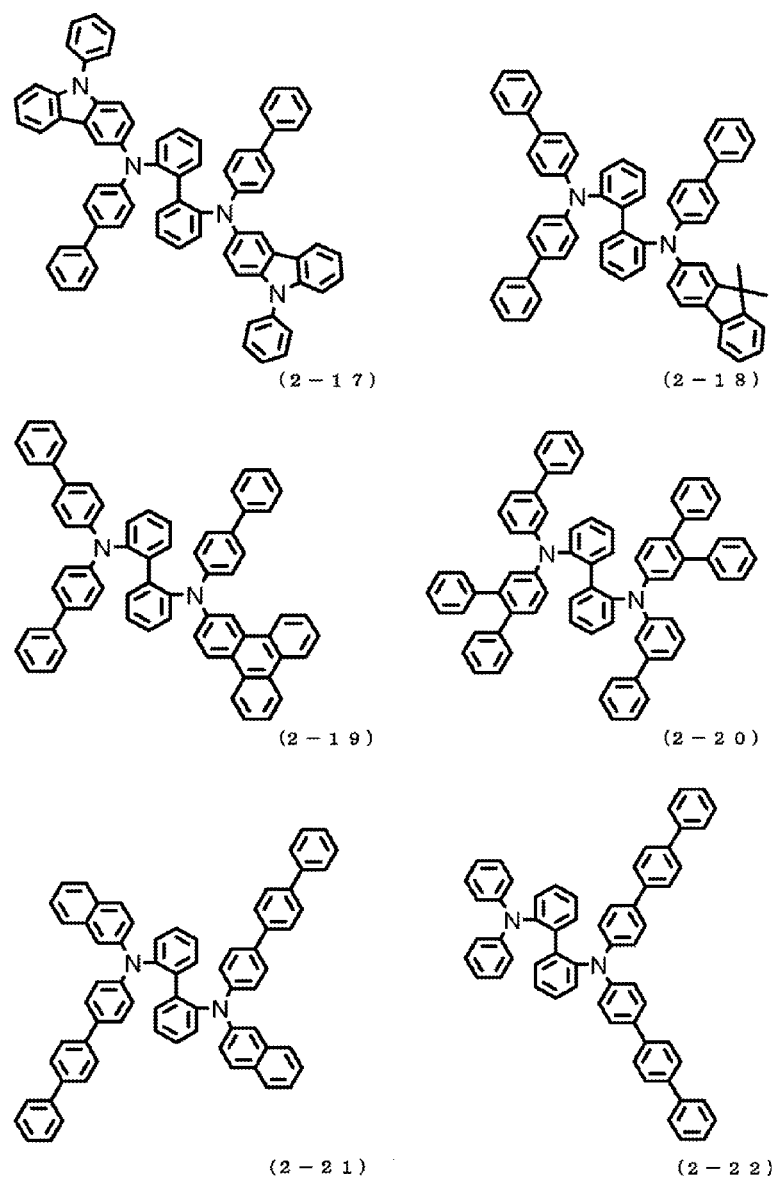
FIG. 12 illustrates structural formulae of Compounds 2-17 through 2-22 which are the aryldiamine compounds.
Figure 13:
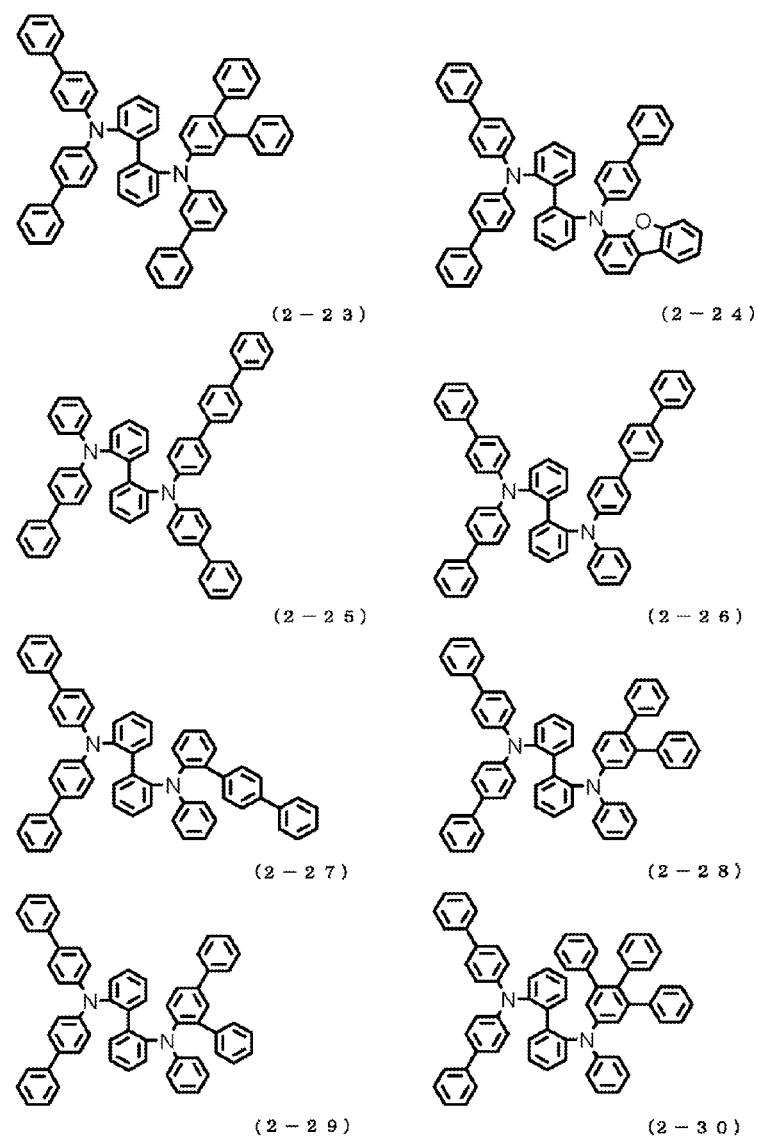
FIG. 13 illustrates structural formulae of Compounds 2-23 through 2-30 which are the aryldiamine compounds.
Figure 14:
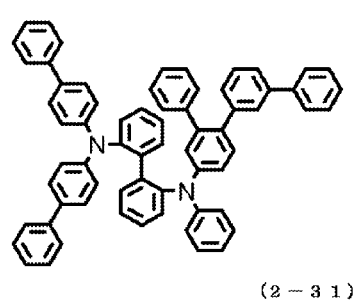
FIG. 14 illustrates structural formulae of Compounds 2-31 through 2-36 which are the aryldiamine compounds.
Figure 14:
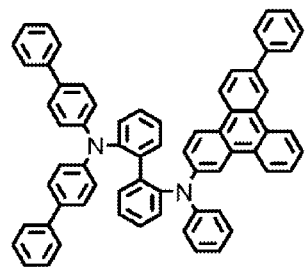
Figure 14:
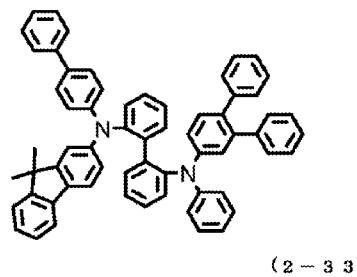
Figure 14:
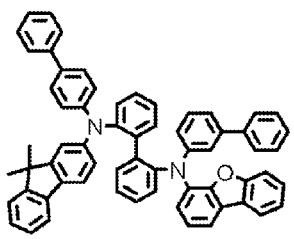
Figure 14:
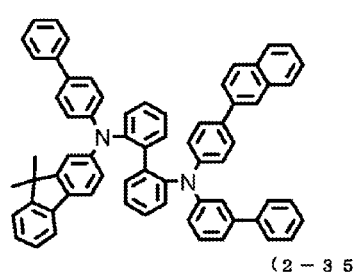
Figure 14:
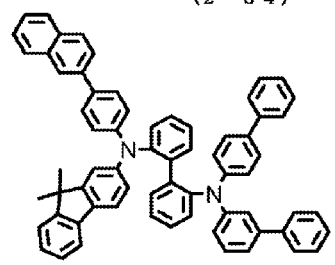
Figure 15:
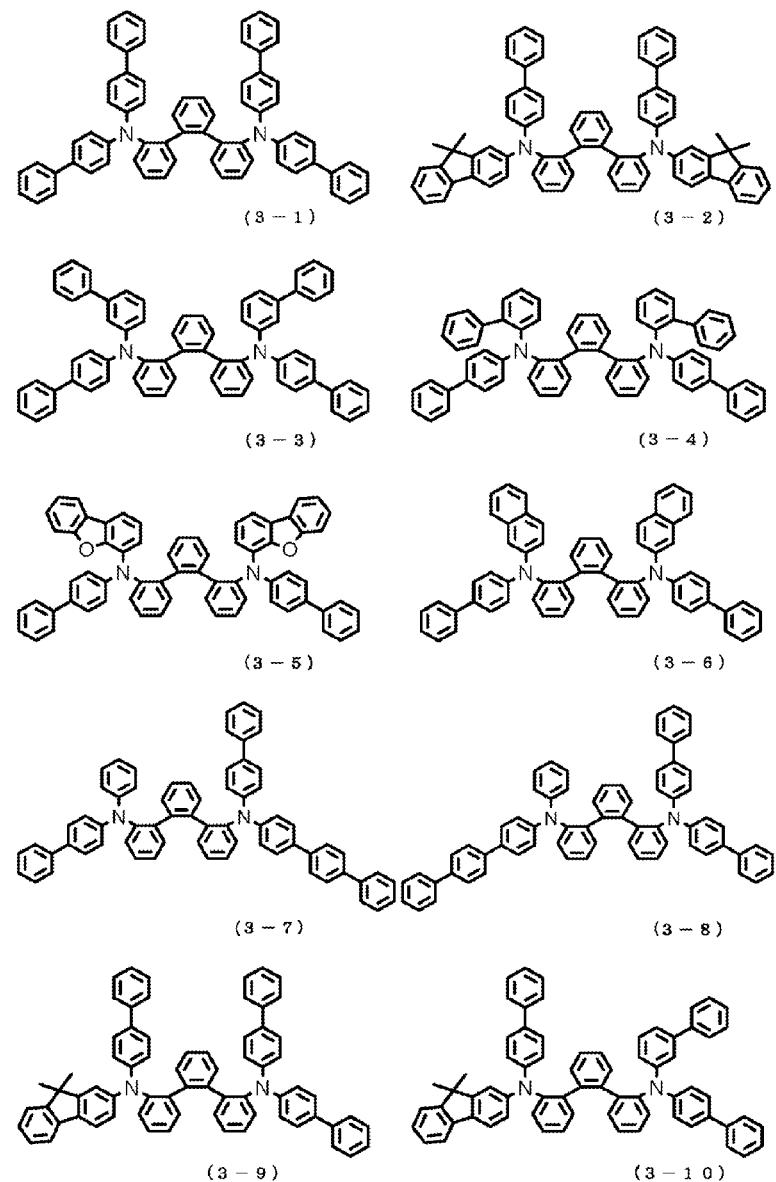
FIG. 15 illustrates structural formulae of Compounds 3-1 to 3-10 which are the aryldiamine compounds.
Figure 16:
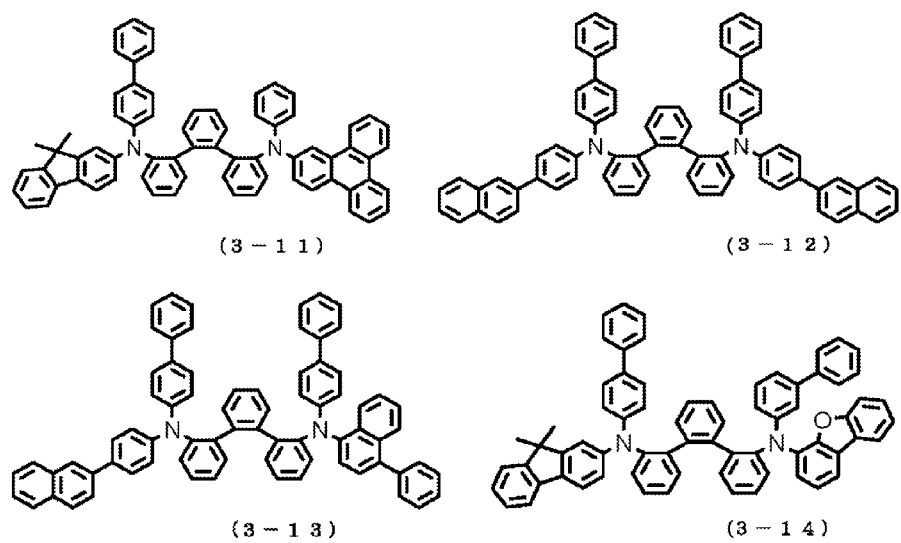
FIG. 16 illustrates structural formulae of Compounds 3-11 through 3-14 which are the aryldiamine compounds.

The organic EL device of the invention may take various configurations as long as it has the above described basic structure. For example, it may be a layer structure which has a substrate, an anode, a hole injection layer, a hole transport layer, an emitting layer, an electron transport layer, and a cathode stacked in that order. It may additionally have an electron blocking layer between the hole transport layer and the emitting layer, a hole blocking layer between the emitting layer and the electron transport layer, or an electron injection layer between the electron transport layer and the cathode. Furthermore, some organic layers may be omitted, or some functions may be performed by a single organic layer. For example, an organic layer may combine features of the hole injection layer and hole transport layer or may combine features of the electron injection layer and electron transport layer. It is also possible that two or more organic layers having the same function may be stacked one on another. For example, the organic EL device may have a duel hole transport layer, a dual emitting layer, a dual electron transport layer, and the like. The organic EL device of the invention preferably has a dual hole transport layer composed of a first hole transport layer and a second hole transport layer. FIG. 4 illustrates the stacked layer structure adopted in Examples described layer, which is composed of a glass substrate 1, a transparent anode 2, a hole injection layer 3, a first hole transport layer 4, a second hole transport layer 5, an emitting layer 6, an electron transport layer 7, an electron injection layer 8, and a cathode 9 in the order described.

While the individual layers will be described layer in detail, note that the organic EL device of the invention is characterized by containing the aryldiamine compound in at least one organic layer.

Anode:

The anode 2 may be formed of any electrode materials known per se. For example, electrode materials with large work functions, such as ITO and gold, are used.

Hole Injection Layer:

The hole injection layer 3 may preferably contain the aryldiamine compound of the invention. Other known materials may be used in place of, or in admixture or combination with, the aryldiamine compound.

Examples of useful known materials include star-burst triphenylamine derivatives and various triphenylamine tetramers; porphyrin compounds typified by copper phthalocyanine; acceptor type heterocyclic compounds, such as hexacyanoazatriphenylene; and solution-processed polymeric materials.

A material commonly used to form the hole injection layer and having been p-doped with trisbromophenylamine hexachloroantimony; a radialene derivative (see WO 2014/009310), or the like; or a polymer having the structure of a benzidine derivative, such as TPD, as a partial structure thereof may also be used.

The hole injection layer 3 can be formed by thin film formation processes, such as evaporation deposition, spin coating, and ink-jet printing, using the material described above. Similarly, other layers described below can each be formed by known thin film formation processes, such as evaporation deposition, spin coating, and ink-jet printing.

Hole Transport Layer:

A hole transport layer is provided on the hole injection layer 3. The hole transport layer may be a single layer but is preferably a stacked dual layer composed of a first hole transport layer 4 on the side of the hole injection layer and a second hole transport layer 5 on the side of the emitting layer.

The hole transport layer preferably contains the aryldiamine compound of the invention. Where the hole transport layer has a dual layer structure, the aryldiamine compound of the invention may be used in either one or both of the two layers under the condition that the two layers are different in composition.

The aryldiamine compound of the invention may be replaced with, or used in admixture or combination with, known materials, such as benzidine derivatives, e.g., N,N'-diphenyl-N,N'-di(m-tolyl)benzidine(TPD), N,N-diphenyl-N,N'-di(t-naphthyl)benzidine (NPD), N,N,N',N'-tetrabiphenylylbenzidine, and 1,1-bis[4-(di-4-tolylamino)phenyl]cyclohexane (TAPC); and trimers and tetramers of various triphenylamine compounds.

The hole transport layer may be formed of a single material or a mixture of materials including the single material. The hole transport layer may have a multi-layer structure composed of (a) layers each formed of a single material, (b) layers each formed of a mixture of materials, or (c) a layer formed of a single material and a layer formed of a mixture of materials. The same structure is applicable to organic layers other than the hole transport layer.

A hole injection/transport layer may be formed using a solution-processed polymer, such as poly(3,4-ethylenedioxythiophene)/poly(styrene sulfonate) (PEDOT/PSS).

A material commonly used to make the hole transport layer and having been p-doped with trisbromophenylamine hexachloroantimony, a radialene derivative (see WO 2014/009310), or the like, or a polymer having the structure of a benzidine derivative, such as TPD, as a partial structure thereof may also be used.

Electron Blocking Layer:

The aryldiamine compound of the invention is also suited to form an electron blocking layer (not shown). Other known electron blocking materials are also useful, including carbazole derivatives, such as 4,4',4"-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz); and triarylamines compounds having a triphenylsilyl group, such as 9-[4-(carbazol-9-yl)phenyl]-9-[4-(tolyphenylsilyl)phenyl]-9H-fluorene.

Emitting Layer:

The aryldiamine compound is also suitable to make the emitting layer 6. Other known light-emitting materials are also useful. Examples of the known materials include quinolinol derivative metal complexes, such as $Alq_3$, other various metal complexes, anthracene derivatives, bisstyrylbenzene derivatives, pyrene derivatives, oxazole derivatives, and poly(p-phenylenevinylene) derivatives.

The emitting layer 6 may be formed of a host material and a dopant material. Examples of the host material include: the aryldiamine compound of the invention, the above described light-emitting materials; heterocyclic compounds having an indole ring as a part of their fused ring system; heterocyclic compounds having a carbazole ring as a part of their fused ring system; carbazole derivatives; thiazole derivatives; benzimidazole derivatives; polydialkylfuorene derivatives; and anthracene derivatives. Examples of the dopant material include amine derivatives having a fluorene ring as a part of their fused ring system; quinacridone, coumarin, rubrene, perylene, pyrene, and their derivatives; benzopyran derivatives; indenophenanthrene derivatives; rhodamine derivatives; and aminostyryl derivatives.

Phosphorescent materials are also useful as a light-emitting material. The phosphorescent materials include iridium complexes and platinum complexes. Examples of the phosphorescent materials include green phosphorescent materials, such as $Ir(ppy)_3$, blue phosphorescent materials, such as FIrpic and FIr6, and red phosphorescent materials, such as $Btp_2Ir(acac)$.

The host material to be doped by the phosphorescent material include carbazole derivatives, such as 4,4'-di(N-carbazolyl)biphenyl (CBP), TCTA, and mCP, as hole injecting/transporting host materials; and p-bis(triphenylsilyl)benzene (UGH2) and 2,2',2"-(1,3,5-phenylene)-tris(1-phenyl-1H-benzimidazole) (TPBI) as electron transporting host materials. Use of such hot materials provides high-performance organic EL derives.

Doping of the host material with the phosphorescent material is preferably carried out by co-depositing the phosphorescent material in an amount ranging from 1 to 30 wt % relative to the whole emitting layer so as to avoid concentration quenching.

A delayed fluorescence emitter, including CDCB derivatives, such as PIC-TRZ, CC2TA, PXZ-TRZ, and 4CzIPN, may also be used as a light-emitting material.

Hole Blocking Layer:

A hole blocking layer (not shown) may be provided on the emitting layer 5. The hole blocking layer may be formed of a known compound having a hole blocking effect. Examples of such a known compound include phenanthroline derivatives, such as bathocuproine (BCP); quinolinol derivative metal complexes, such as aluminum (III) 4-biphenylolate 2-methyl-8-quinolinolate (BAlq); various rare earth complexes; triazole derivatives; triazine derivatives; and oxadiazole derivatives. These materials may also serve as a material of the electron transport layer.

Electron Transport Layer:

The electron transport layer 7 may be formed of a known electron transporting material. Examples of useful known electron transporting materials include quinolinol derivative metal complexes, such as $Alq_3$ and BAlq; other various metal complexes; triazole derivatives; triazine derivatives; oxadiazole derivatives; pyridine derivatives; pyrimidine derivatives; benzimidazole derivatives; thiadiazole derivatives; anthracene derivatives; carbodiimide derivatives; quinoxaline derivatives; pyridoindole derivatives; phenanthroline derivatives; and silole derivatives.

Electron Injection Layer:

The electron injection layer 8 may be formed of, for example, an alkali metal salt, such as lithium fluoride or cesium fluoride; an alkaline earth metal salt, such as magnesium fluoride; or a metal oxide, such as aluminum oxide. As long as the materials of the electron transport layer and the cathode are suitably chosen, the electron injection layer may be omitted.

Cathode:

The cathode 9 may be formed of an electrode material with a low work function, such as aluminum, or an alloy with a still lower work function, such as magnesium-silver alloy, magnesium-indium alloy, or aluminum-magnesium alloy.

EXAMPLES

The invention will now be illustrated in greater detail with reference to Examples, but it should be understood that the invention is not construed as being limited thereto.

Example 1—Compound 1-2

Synthesis of 1,2-bis[biphenyl-4-yl(9,9-dimethyl-9H-fluoren-2-yl)amino]benzene

In a reaction vessel purged with nitrogen were put 24.1 g of biphenyl-4-yl(9,9-dimethyl-9H-fluoren-2-yl)amine, 10.0 g of 1,2-diiodobenzene, 0.2 g of copper powder, 10.5 g of potassium carbonate, and 10 ml of dodecylbenzene. The mixture was stirred under reflux for 72 hours. The resulting reaction mixture was cooled, toluene added thereto to conduct extraction, and the extract filtered to remove insoluble solid, followed by concentration. The concentrate was purified by column chromatography using silica gel as stationary phase and toluene/n-heptane as eluent. The eluate was purified by recrystallization from a $CH_2Cl_2$/acetone mixed solvent to give 15.7 g (yield: 65.0%) of Compound 1-2 as white powder.

The white powder was analyzed by NMR analysis to identify the structure. As a result, the following 48 signals of hydrogen were observed in $^1$H-NMR (DMSO-$d_6$). δ (ppm)=7.65 (4H), 7.49-7.18 (24H), 6.86-6.78 (8H), and 1.29 (12H)

[Chem. 16]

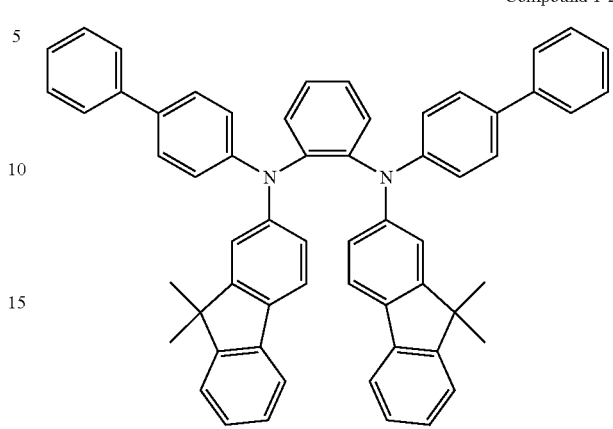

Compound 1-2

Example 2—Compound 2-1

Synthesis of 2,2'-bis[di-(4-biphenyl)amino]biphenyl

In a reaction vessel purged with nitrogen were put 13.9 g of bis(4-biphenyl)amine, 8.0 g of 2,2'-diiodobiphenyl, 0.1 g of copper powder, 6.8 g of potassium carbonate, and 10 ml of dodecylbenzene. The mixture was stirred under reflux for 72 hours, the reaction mixture cooled, toluene added for extraction to remove insoluble matter, the extract filtered, and the filtrate concentrated. The concentrate was purified by recrystallization from a toluene/acetone mixed solvent to yield 10.9 g (70.0%) of Compound 2-1 as white powder.

The structure of the resulting white powder was identified by NMR analysis. As a result, the following 44 signals of hydrogen were detected in $^1$H-NMR (DMSO-$d_6$). δ (ppm) =7.50 (8H), 7.39-7.30 (14H), 7.28-7.25 (10H), 6.96 (4H), and 6.76 (8H).

[Chem. 17]

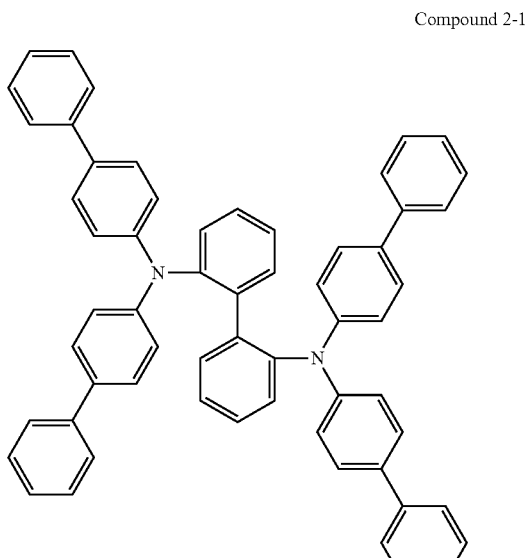

Compound 2-1

Example 3—Compound 2-4

Synthesis of 2,2'-bis[biphenyl-4-yl-(9,9-dimethyl-9H-fluoren-2-yl)amino]biphenyl In a reaction vessel purged with nitrogen were put 15.7 g of biphenyl-4-yl(9,9-dimethyl-9H-fluoren-2-yl)amine, 8.0 g of 2,2'-diiodobiphenyl, 0.1 g of copper powder, 6.8 g of potassium carbonate, and 10 ml of dodecylbenzene. The mixture was stirred under reflux for one week, the reaction mixture cooled, toluene added for extraction to remove insoluble matter, the extract filtered, and the filtrate concentrated. The concentrate was purified by recrystallization from acetone to yield 12.7 g (73.8%) of Compound 2-4 as white powder.

The structure of the resulting white powder was identified by NMR analysis. As a result, the following 52 signals of hydrogen were detected in $^1$H-NMR (DMSO-d$_6$). δ (ppm)=7.66 (2H), 7.57 (2H), 7.48-7.14 (24H), 7.02 (2H), 6.83-6.64 (10H), 1.29 (6H), and 1.02 (6H).

[Chem. 18]

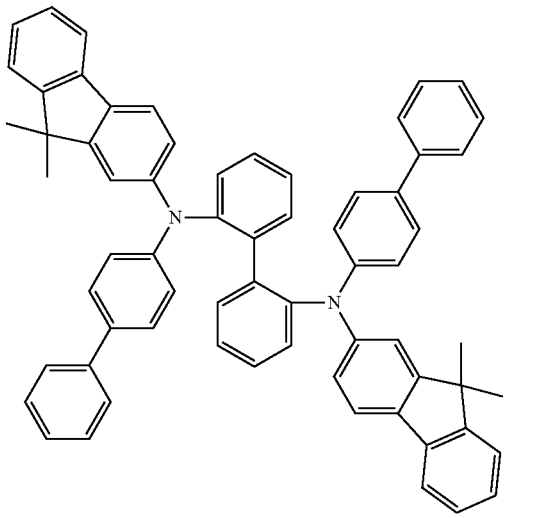

Compound 2-4

The melting temperature and glass transition temperature of the compounds prepared in Examples were determined using a high-sensitivity differential scanning calorimeter (DSC 3100SA, from Bruker AXS).

|  | Melting Temp. (° C.) | Glass Transition Temperature (° C.) |
|---|---|---|
| Compound 1-2 (Example 1) | ND | 126 |
| Compound 2-1 (Example 2) | 248 | 123 |
| Compound 2-4 (Example 3) | ND | 146 |

It is seen that the aryldiamine compounds of the invention have a glass transition temperature of 100° C. or higher and are therefore stable in thin film form.

A 100 nm thick film was deposited on an ITO substrate by evaporation of each of the compounds obtained in Examples. The work function of the film was determined using an ionization potential measuring device (PYS-202, available from Sumitomo Heavy Industries, Ltd.).

|  | Work Function (eV) |
|---|---|
| Compound 1-2 of Example 1 | 5.62 |
| Compound 2-1 of Example 2 | 5.71 |
| Compound 2-4 of Example 3 | 5.69 |

It is seen that the aryldiamine compounds of the invention exhibit suitable energy levels as compared with commonly used hole transporting materials with a work function of 5.4 eV, such as NPD and TPD, and therefore have good hole transporting ability.

Device Example 1

A glass substrate 1 having an ITO electrode as a transparent anode 2 formed thereon beforehand was provided. A hole injection layer 3, a first hole transport layer 4, a second hole transport layer 5, an emitting layer 6, an electron transport layer 7, an electron injection layer 8, and a cathode 9 (aluminum electrode) were evaporation-deposited on the ITO substrate in the order described in FIG. 4 to make an organic EL device.

More specifically, a glass substrate 1 with a 150 nm-thick ITO layer was cleaned with isopropyl alcohol under ultrasonication for 20 minutes. After drying on a hot plate heated to 200° C. for 10 minutes, the ITO glass substrate was further cleaned by UV/ozone for 15 minutes. The thus cleaned ITO glass substrate was set in a vacuum deposition chamber, and the chamber was evacuated to 0.001 Pa or lower.

Compound HIM-1 shown below was evaporation-deposited to cove the transparent anode 2 to form a 5 nm thick hole injection layer 3.

[Chem. 19]

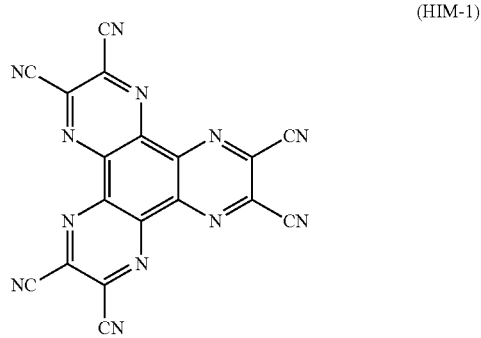

(HIM-1)

On the hole injection layer 3 was evaporation-deposited a triphenylamine derivative HTM-1 shown below to form a 60 nm thick first hole transport layer 4.

[Chem. 20]

(HTM-1)

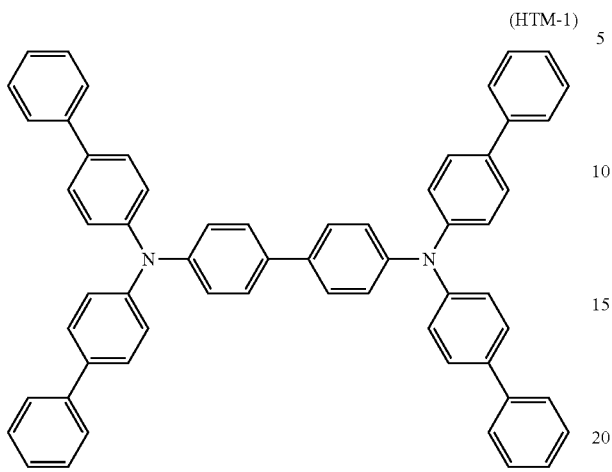

On the first hole transport layer 4 was evaporation-deposited Compound 1-2 of Example 1 to form a 5 nm thick second hole transport layer 5.

[Chem. 21]

Compound 1-2

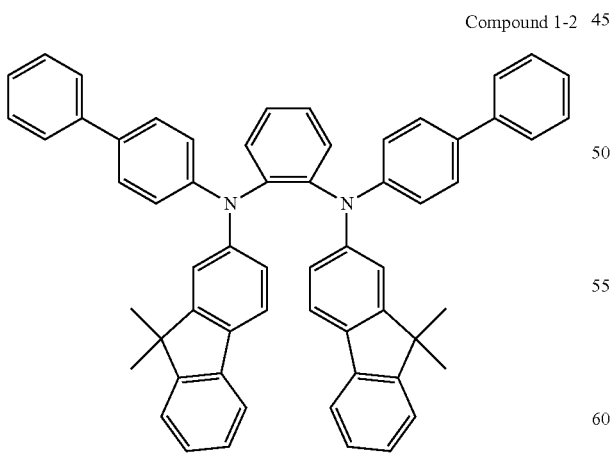

On the second hole transport layer 5 were co-deposited an iridium complex EMD-1 shown below and a carbazole derivative EMH-1 below at an EMD-1:ETH-1 deposition rate ratio of 5:95 to form a 20 nm thick emitting layer 6.

[Chem. 22]

(EMD-1)

(EMH-1)

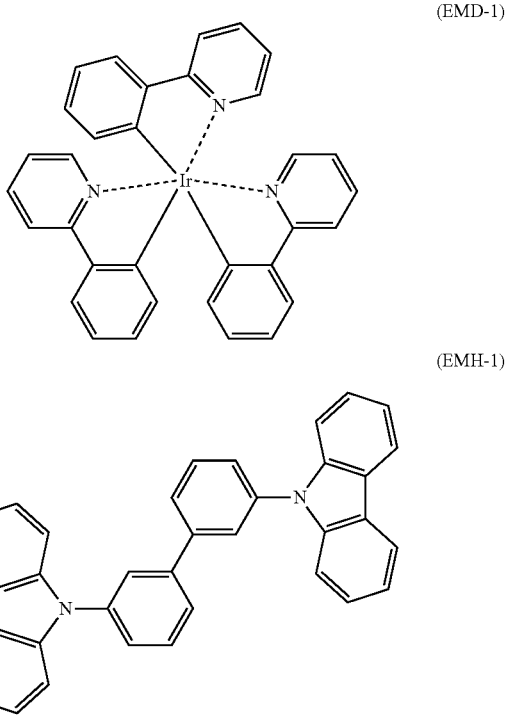

On the emitting layer 6 were co-deposited a pyrimidine compound ETM-1 below and a compound ETM-2 below at an ETM-1:ETM-2 deposition rate ratio of 50:50 to form a 30 nm thick electron transport layer 7.

[Chem. 23]

(ETM-1)

(ETM-2)

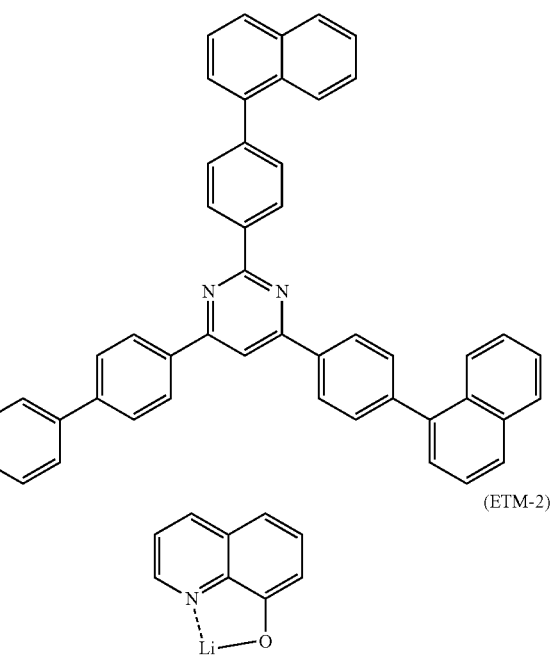

Lithium fluoride was evaporation-deposited on the electron transport layer 7 to form a 1 nm thick electron injection layer 8.

Finally, aluminum was deposited on the electron injection layer 8 to form a 100 nm thick cathode 9.

Device Example 2

An organic EL device was fabricated in the same manner as in Device Example 1, except that the second hole transport layer 5 was formed using Compound 2-1 of Example 2 in place of Compound 1-2 of Example 1.

[Chem. 24]

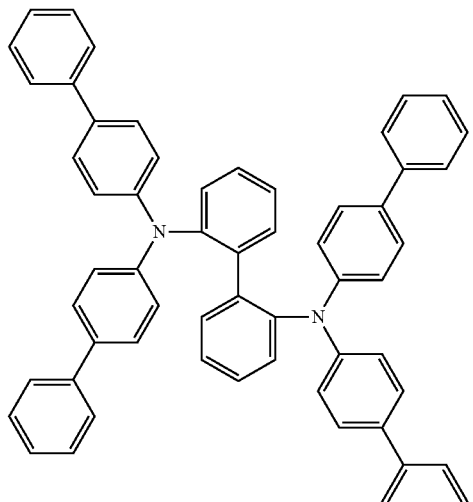

Compound 2-1

Device Example 3

An organic EL device was fabricated in the same manner as in Device Example 1, except that the second hole transport layer 5 was formed using Compound 2-4 of Example 3 in place of Compound 1-2 of Example 1.

[Chem. 25]

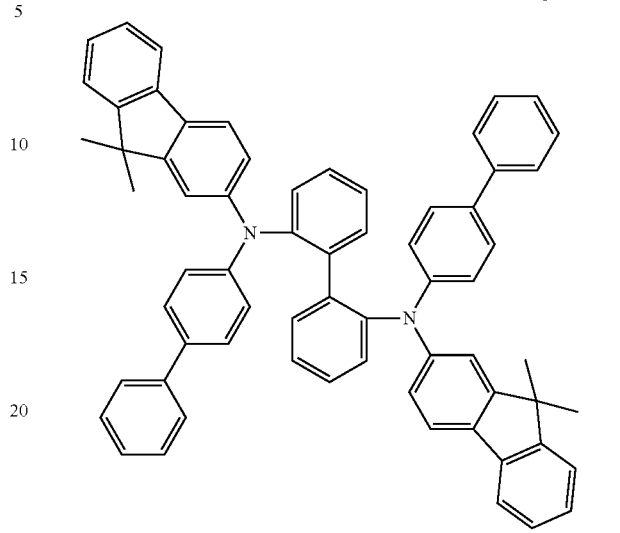

Compound 2-4

Comparative Device Example 1

For comparison, an organic EL device was fabricated in the same manner as in Device Example 1, except that the second hole transport layer 5 was formed using HTM-2 shown below in place of Compound 1-2 of Example 1.

[Chem. 26]

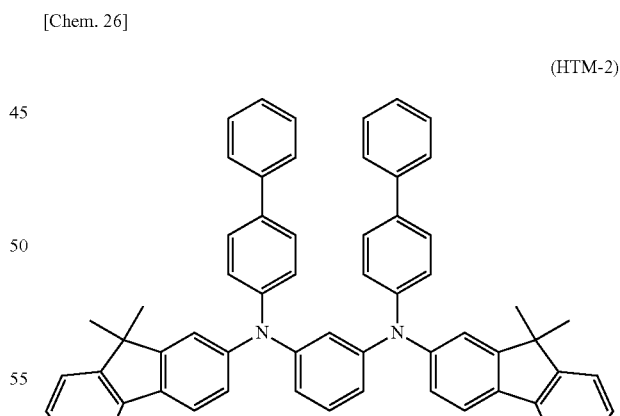

(HTM-2)

Comparative Device Example 2

For comparison, an organic EL device was fabricated in the same manner as in Device Example 2, except that the second hole transport layer 5 was formed using HTM-3 shown below in place of Compound 2-1 of Example 2.

[Chem. 27]

(HTM-3)

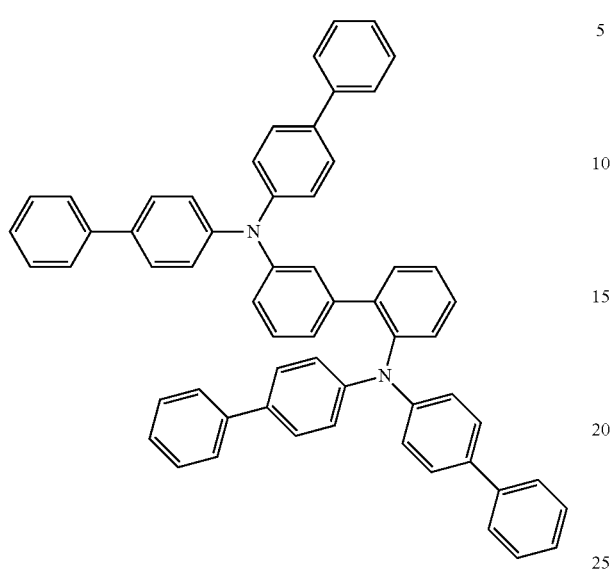

Comparative Device Example 3

For comparison, an organic EL device was fabricated in the same manner as in Device Example 2, except that the second hole transport layer 5 was formed using HTM-4 shown below in place of Compound 2-1 of Example 2.

[Chem. 28]

(HTM-4)

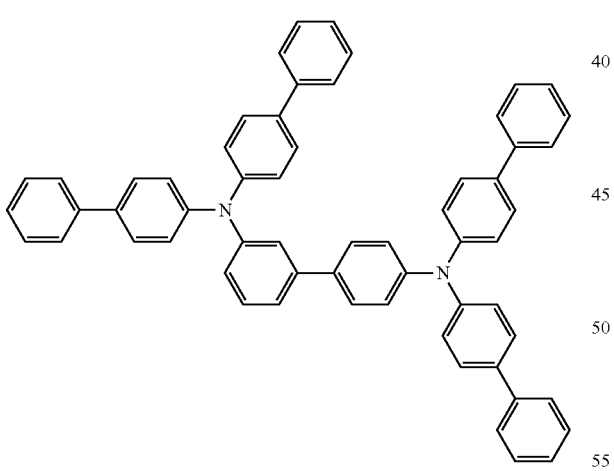

Comparative Device Example 4

For comparison, an organic EL device was fabricated in the same manner as in Device Example 2, except that the second hole transport layer 5 was formed using HTM-5 shown below in place of Compound 2-1 of Example 2.

[Chem. 29]

(HTM-5)

The organic EL devices made in Device Examples 1 to 3 and Comparative Device Examples 1 to 4 were evaluated for characteristics in the atmosphere at ambient temperature. Emission characteristics of each device when a direct voltage was applied were determined. The results obtained are shown in Table 1 below.

The life of the organic EL devices made in Device Examples 1 to 3 and Comparative Device Examples 1 to 4 was determined as follows. Each EL device was driven at a constant current that resulted in an initial luminance (the luminance at the onset of light emission) of 9000 cd/m$^2$. The time required for the initial luminance to decay to 8550 cd/m$^2$ (95% of the initial luminance) was recorded. The results are shown in Table 1.

TABLE 1

| | 2nd Hole Transport Layer | Voltage (V) (@10 mA/cm$^2$) | Luminance (cd/m$^2$) (@10 mA/cm$^2$) | Emission Efficiency (cd/A) (@10 mA/cm$^2$) | Power Efficiency (lm/W) (@10 mA/cm$^2$) | Life (h) (95% decay) |
|---|---|---|---|---|---|---|
| Device Example 1 | Compound 1-2 | 4.12 | 7200 | 72.05 | 54.95 | 200 |
| Device Example 2 | Compound 2-1 | 4.30 | 7769 | 77.77 | 56.82 | 340 |
| Device Example 3 | Compound 2-4 | 4.12 | 7629 | 76.41 | 58.34 | 337 |
| Comparative Device Example 1 | HTM-2 | 4.20 | 6990 | 69.95 | 52.33 | 111 |

TABLE 1-continued

| | 2nd Hole Transport Layer | Voltage (V) (@10 mA/cm$^2$) | Luminance (cd/m$^2$) (@10 mA/cm$^2$) | Emission Efficiency (cd/A) (@10 mA/cm$^2$) | Power Efficiency (lm/W) (@10 mA/cm$^2$) | Life (h) (95% decay) |
|---|---|---|---|---|---|---|
| Comparative Device Example 2 | HTM-3 | 4.28 | 7291 | 73.00 | 53.59 | 216 |
| Comparative Device Example 3 | HTM-4 | 4.20 | 7065 | 70.70 | 52.89 | 305 |
| Comparative Device Example 4 | HTM-5 | 4.45 | 7424 | 74.31 | 52.47 | 200 |

Comparing the organic EL devices of Device Example 1 and Comparative Device Example 1, in which the aryldiamine compounds used to form the second hole transport layer 5 were structurally similar except for the phenylene group linking the two amino groups, the emission efficiency of the device of Comparative Device Example 1 was 69.95 cd/A with a current density of 10 mA/cm$^2$ applied, whilst that of the device of Device Example 1 was as high as 72.05 cd/A.

The power efficiency of the organic EL device of Comparative Device Example 1 was 52.33 lm/W, whereas that of the device of Device Example 1 was as high as 54.95 lm/W.

The life (95% decay) of the organic EL device of Comparative Device Example 1 was 111 hours, whilst the device of Device Example 1 showed a remarkable extension of life to as long as 200 hours.

Similarly, when comparing the organic EL devices of Device Example 2 and Comparative Device Examples 2 to 4, in which the aryldiamine compounds used to form the second hole transport layer 5 were structurally similar except for the biphenylene group linking the two amino groups, the emission efficiency of the devices of Comparative Device Examples 2 to 4 was between 70.70 cd/A and 74.31 cd/A with a current density of 10 mA/cm$^2$ applied, while that of the device of Device Example 2 was as high as 77.77 cd/A.

The power efficiency of the organic EL devices of Comparative Device Examples 2 to 4 was from 52.47 to 53.59 lm/W, whereas that of the device of Device Example 2 was as high as 56.82 lm/W.

The life (95% decay) of the organic EL devices of Comparative Device Examples 2 to 4 was 200 to 305 hours, whereas the device of Device Example 2 showed an extension of life to as long as 340 hours.

Similarly, on comparing the organic EL devices of Device Examples 2 and 3, in which the aryldiamine compounds used to form the second hole transport layer 5 were structurally the same except for Ar$^2$ and Ar$^3$ in formula (1), it is seen that the organic EL device of Device Example 2, in which Ar$^2$ and Ar$^3$ in formula (1) were each an aromatic hydrocarbon group having a fused polycyclic structure, exhibited a higher emission efficiency and a longer life than that of Device Example 3, in which Ar$^2$ and Ar$^3$ in formula (1) were each an aromatic hydrocarbon group having no fused polycyclic structure.

The above results prove that the organic EL device using the aryldiamine compound of the invention achieves a higher emission efficiency and a longer life than conventional organic EL devices.

INDUSTRIAL APPLICABILITY

The aryldiamine compound of the invention exhibits high hole transporting properties and high electron blocking properties and is stable in its thin film form and is therefore excellent as a material for fabricating organic EL devices. The organic EL device of the invention, which is fabricated by using the compound of the invention, exhibits high emission efficiency and high power efficiency, requires a low driving voltage, and shows excellent durability. Therefore, the organic EL device of the invention is promising for application to home appliances and lighting equipment.

REFERENCE SIGNS LIST

1: Glass substrate
2: Transparent anode
3: Hole injection layer
4: First hole transport layer
5: Second hole transport layer
6: Emitting layer
7: Electron transport layer
8: Electron injection layer
9: Cathode

The invention claimed is:
1. An aryldiamine compound represented by formula (1-1b) or (1-2b):

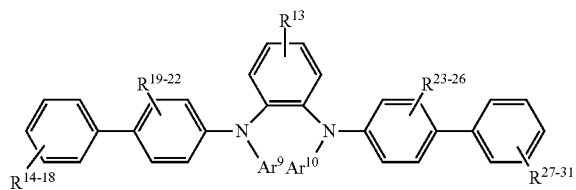

(1-1b)

wherein Ar$^9$ and Ar$^{10}$ each represent an unsubstituted or substituted fluorenyl group;
R$^{13}$ represents a hydrogen atom or a deuterium atom;
R$^{14-18}$ represents multiple groups R$^{14}$, R$^{15}$, R$^{16}$, R$^{17}$, and R$^{18}$ bonded to the benzene ring at different positions;
R$^{19-22}$ represents multiple groups R$^{19}$, R$^{20}$, R$^{21}$, and R$^{22}$ bonded to the benzene ring at different positions;
R$^{23-26}$ represents multiple groups R$^{23}$, R$^{24}$, R$^{25}$, and R$^{26}$ bonded to the benzene ring at different positions;
R$^{27-31}$ represents multiple groups R$^{27}$, R$^{28}$, R$^{29}$, R$^{30}$, and R$^{31}$ bonded to the benzene ring at different positions; and
R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, and R$^{31}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group;

(1-2b)

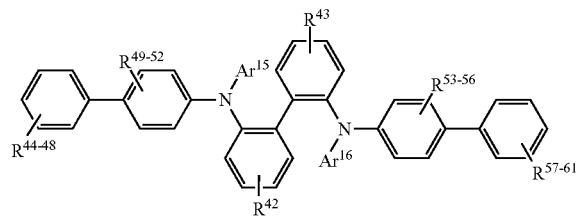

wherein $Ar^{15}$ and $Ar^{16}$ each represent an aromatic hydrocarbon group having two or more aromatic rings;

$R^{42}$ and $R^{43}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group;

$R^{44-48}$ represents multiple groups $R^{44}$, $R^{45}$, $R^{46}$, $R^{47}$, and $R^{48}$ bonded to the benzene ring at different positions;

$R^{49-52}$ represents multiple groups $R^{49}$, $R^{50}$, $R^{51}$, and $R^{52}$ bonded to the benzene ring at different positions;

$R^{53-56}$ represents multiple groups $R^{53}$, $R^{54}$, $R^{55}$, and $R^{56}$ bonded to the benzene ring at different positions;

$R^{57-61}$ represents multiple groups $R^{57}$, $R^{58}$, $R^{59}$, $R^{60}$, and $R^{61}$ bonded to the benzene ring at different positions; and $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, an $R^{61}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkoxy group having 1 to 6 carbon atoms, a cycloalkoxy group having 5 to 10 carbon atoms, an aromatic hydrocarbon group, an aromatic heterocyclic group, or an aryloxy group.

2. An organic electroluminescent device comprising a pair of electrodes and at least one organic layer disposed between the pair of electrodes, wherein the at least one organic layer comprises the aryldiamine compound according to claim 1.

3. The organic electroluminescent device according to claim 2, wherein the at least one organic layer contains a hole transporting layer.

4. The organic electroluminescent device according to claim 2, wherein the at least one organic layer contains an electron blocking layer.

5. The organic electroluminescent device according to claim 2, wherein the at least one organic layer contains a hole injection layer.

6. The organic electroluminescent device according to claim 2, wherein the at least one organic layer contains an emission layer.

7. The organic electroluminescent device according to claim 3, wherein the hole transporting layer is a dual layer composed of a first hole transport layer and a second hole transport layer.

* * * * *